(12) United States Patent
Lee et al.

(10) Patent No.: US 12,123,872 B2
(45) Date of Patent: Oct. 22, 2024

(54) CONCENTRATION KIT FOR LATERAL FLOW ASSAY STRIP

(71) Applicant: Calth. Inc., Gyeonggi-do (KR)

(72) Inventors: Jeong Hoon Lee, Gyeonggi-do (KR); Yong Kyoung Yoo, Seoul (KR); Sung Il Han, Seoul (KR); Cheon Jung Kim, Seoul (KR)

(73) Assignee: Calth, Inc., Seongnam-Si (KR)

( * ) Notice: Subject to any disclaimer, the term of this patent is extended or adjusted under 35 U.S.C. 154(b) by 1559 days.

(21) Appl. No.: 16/461,900

(22) PCT Filed: Nov. 16, 2017

(86) PCT No.: PCT/KR2017/013032
§ 371 (c)(1),
(2) Date: May 17, 2019

(87) PCT Pub. No.: WO2018/093175
PCT Pub. Date: May 24, 2018

(65) Prior Publication Data
US 2019/0331563 A1    Oct. 31, 2019

(30) Foreign Application Priority Data

Nov. 18, 2016  (KR) .................. 10-2016-0154353
Feb. 2, 2017   (KR) .................. 10-2017-0014823

(51) Int. Cl.
| | |
|---|---|
| G01N 33/543 | (2006.01) |
| B01L 3/00 | (2006.01) |
| G01N 1/40 | (2006.01) |
| G01N 33/538 | (2006.01) |
| G01N 33/549 | (2006.01) |
| G01N 33/563 | (2006.01) |

(52) U.S. Cl.
CPC .. G01N 33/54388 (2021.08); B01L 3/502761 (2013.01); G01N 1/40 (2013.01); G01N 33/538 (2013.01); G01N 33/54393 (2013.01); G01N 33/549 (2013.01); G01N 33/563 (2013.01)

(58) Field of Classification Search
None
See application file for complete search history.

(56) References Cited

U.S. PATENT DOCUMENTS

2007/0134811 A1* 6/2007 Takeuchi ............. G01N 33/558
                                                           436/514

FOREIGN PATENT DOCUMENTS

| EP | 2128617 | * 12/2009 | ........... G01N 33/543 |
|---|---|---|---|
| KR | 20150083722 A | 7/2015 | |
| KR | 20150130346 A | 11/2015 | |
| KR | 20160090661 A | 8/2016 | |
| WO | WO 2006094056 | * 9/2006 | |
| WO | WO 2014165618 | * 10/2014 | ............... C12Q 1/00 |
| WO | WO 2015184465 | * 12/2015 | ............... C12Q 1/00 |

OTHER PUBLICATIONS

Gong et al., "Nanoporous Membranes Enable Concentration and Transport in Fully Wet Paper-Based Assays", Analytical Chemistry, 2014, pp. 8090-8097.*
Phan et al. "Sample concentration in a microfluidic paper-based analytical device using ion concentration polarization", Sensors and Actuators B 222 (2016) 735-740.*
PCT International Search Report in PCT/KR2017/013032 dated Nov. 18, 2016. 5 pages.
Chang, Chih-Chang , et al., "Ion concentration polarization near microchannel-nanochannel interfaces: Effect of pH value", Electrophoresis Journal 2012, 33, Nov. 25, 2011, 758-764.
Gong, Max M., et al., "Direct DNA Analysis with Paper-Based Ion Concentration Polarization", American Chemical Society, Oct. 8, 2015, 13913-13919.
Gong, Max M., et al., "Nanoporous Membranes Enable Concentration and Transport in Fully Wet Paper-Based Assays", ACS Publications, Jul. 21, 2014, 8090-8097.
Han, Sung Il, et al., "Microfluidic paper-based biomolecule preconcentrator based on ion concentration polarization", Lab Chip, 2016, 16, May 5, 2016, 2219-2227.
Jeon, Hyungkook , et al., "Ion concentration polarization-based continuous separation device using electrical repulsion in the depletion region", Scientific Reports | 3 : 3483, Dec. 19, 2013, 1-6.
Kim, Cheonjung , et al., "Battery operated preconcentration-assisted lateral flow assay", Royal Society of Chemistry, Lab Chip, 2017, 17, 2451, May 31, 2017, 2451-2458.
Kim, Sung Kim, et al., "Direct seawater desalination by ion concentration polarization", Nature Nanotechnology | vol. 5 | Apr. 2010, Mar. 21, 2010, 297-301.
Kim, Sung Jae, et al., "Nanofluidic concentration devices for biomolecules utilizing ion concentration polarization: theory, fabrication, and applications", The Royal Society of Chemistry 2010, 39, Jan. 4, 2010, 912-922.
Kim, Pilnam , et al., "Stabilization of Ion Concentration Polarization Using a Heterogeneous Nanoporous Junction", Nano Letters 2010, 10, Dec. 17, 2009, 16-23.
Ko, Sung Hee, et al., "Nanofluidic preconcentration device in a straight microchannel using ion concentration polarization", Lab Chip, 2012, 12, Jul. 23, 2012, 4472-4482.
Kwak, Rhokyun , et al., "Continuous-Flow Biomolecule and Cell Concentrator by Ion Concentration Polarization", Analytical Chemistry 2011, 83, Aug. 21, 2011, 7348-7355.
Li, Xue , et al., "Microfluidic Paper-Based Sample Concentration Using Ion Concentration Polarization with Smartphone Detection", Micromachines 2016, 7, 199, Nov. 4, 2016, 1-12.

(Continued)

Primary Examiner — Ann Montgomery
(74) Attorney, Agent, or Firm — Servilla Whitney LLC

(57) ABSTRACT

Embodiments of the present invention provide a lateral flow assay method and strip wherein a sample is injected into a sample pad, a preconcentration kit is coupled to the sample pad to preconcentrate analytes, and a conjugate pad or a test pad is connected to the sample pad to transfer the analytes to the conjugate pad or the test pad, whereby a biomarker present at a low concentration can be detected.

14 Claims, 26 Drawing Sheets

(56) References Cited

OTHER PUBLICATIONS

Phan, Dinh-Tuan, et al., "Sample concentration in a microfluidic paper-based analytical deviceusing ion concentration polarization", Elsevier B.V., Sep. 12, 2015, 735-740.

Yang, Ruey-Jen, et al., "Ion concentration polarization on paper-based microfluidic devices and its application to preconcentrate dilute sample solutions", Biomicrofluidics 9, 014122 (2015), Feb. 18, 2015, 1-11.

Yeh, Li-Hsien, et al., "Ion Concentration Polarization in Polyelectrolyte-Modified Nanopores", Journal of Physical Chemistry C 2012, 116, Apr. 4, 2012, 8672-8677.

Zangle, Thomas A., et al., "Theory and experiments of concentration polarization and ion focusing at microchannel and nanochannel interfacesw", The Royal Society of Chemistry 2010, Jan. 29, 2010, 1014-1035.

* cited by examiner

CONCENTRATION KIT FOR LATERAL FLOW ASSAY STRIP

TECHNICAL FIELDS

The embodiments of the present invention relate to an invention in the technical field of a preconcentration kit for lateral flow assay strip.

BACKGROUND

The contents described in this section are simply provided for background information about the embodiments of the present invention and in no way construed as a prior art.

Modern medical science aims not to simply prolong human life, but to realize the extension of healthy life, that is, to live healthier and longer lives. As a result, a paradigm for future medical science shifts from focusing on Treatment Medicine to implementing 3P of Preventive Medicine, Predictive Medicine, and Personalized Medicine. To realize the 3P specifically, early finding and treatment of diseases are becoming very important. For this reason, scientific research on biomarkers has been flourishing.

Biomarkers are indicators that can distinguish between normal and pathological states or conditions, or predict or objectively determine a response to a therapeutic intervention. Biomarkers comprise nucleic acids (DNA, RNA), proteins, lipids, metabolites, or changes in their patterns. In other words, simple substances such as blood glucose for the diagnosis of diabetes mellitus and genes like BCR-ABL fusion gene of chronal myelogenous leukemia, which is a therapeutic target of Glivec® medicine, are all biomarkers and being practically employed in clinical studies.

Development and progression of diseases can be determined by analyzing a nucleic acid or protein. However, technologies and devices for protein analysis are based on nanotechnology which is difficult to be widely available since the manufacturing of such devices are difficult and their prices are relatively high. Further, devices for protein analysis have some disadvantages in that a high-sensitivity sensor is required or it is difficult to do the analysis accurately with a small amount of sample. A typical method for detecting a nucleic acid or protein is a lateral flow assay using a chromatographic method. The lateral flow assay method is being used in a variety of areas including pregnancy testing.

Pregnancy test kits use a monoclonal antibody that binds to human chorionic gonadotropin (HCG). The HCG monoclonal antibody which only reacts with HCG are attached to color-developing materials. HCG in urine is bound to the HCG antibody in the pregnancy test kit to produce a HCG complex which migrates along the kit. When the HCG complex arrives at the pregnancy display window in the kit, the complex is conjugated to an antibody that binds to HCG, resulting in a red-colored band displayed. In the examination completion window in the kit, the HCG antibody to which color-developing materials are attached is conjugated to an antibody that binds to said HCG antibody and a red-colored band appears.

HCGs are normally present at a high concentration and thus easily detectable. Other biomarkers, however, have low concentrations that make them difficult to be detected.

PRIOR ART REFERENCES

Patents (Patent 1) Korean Patent No. 10-1652294 (Granted on Aug. 24, 2016)

SUMMARY OF THE INVENTION

Problems to be Solved

The present invention is mainly aimed at detecting a biomarker at a low concentration by injecting samples into a sample pad, preconcentrating analytes by attaching a preconcentration kit to the sample pad, and transferring the analytes to a conjugate pad by connecting the conjugate pad to the sample pad.

Other unspecified purposes of the present invention can be further considered to the extent that they can be easily inferred from the following detailed explanation and resulting effects.

Solutions of the Problems

In one aspect of the present invention, a lateral flow assay method is provided for using a lateral flow assay strip for detecting analytes in a sample, the method comprising: injecting the sample into a sample pad, preconcentrating the analytes by attaching a preconcentration kit to the sample pad, and transferring the analytes to a conjugate pad or a test pad by connecting the conjugate pad or the test pad to the sample pad.

The method may further comprise separating the conjugate pad from the sample pad prior to injecting the sample into the sample pad.

The preconcentration of the analytes may be carried out by applying an electric field to the preconcentration kit.

After the preconcentration of the analytes, the method may further comprise (i) removing the electric field applied to the preconcentration kit, (ii) connecting the conjugate pad to the sample pad, or (iii) combining these steps.

The method may also comprise separating the preconcentration kit from the sample pad prior to connecting the conjugate pad to the sample pad.

In another aspect of the present invention, a lateral flow assay strip is provided for detecting analytes in a sample, the lateral flow assay strip comprising: a support; a sample pad connected to the support and receiving the sample; and a test pad connected to the support and comprising a captor for capturing the analytes, characterized in that the flow path of the analytes between the sample pad and the test pad is constructed as a blocked structure.

The sample pad may comprise a preconcentration kit, which may comprise at least one selective ion permeable membrane, and electrodes connected to the at least one selective ion permeable membrane.

The preconcentration kit may further comprise a channel in a linear form and a buffer formed apart from the channel, and the selective ion permeable membrane may be configured to connect with the buffer and intersect with the channel.

The selective ion permeable membrane may exist in multiple numbers, and the multiple selective ion permeable membranes may be separately located according to the flow direction of the lateral flow assay strip.

The lateral flow assay strip may further comprise a distance adjustment element for adjusting the distance between the multiple selective ion permeable membranes and displaying the distance.

The preconcentration kit may further contain a power supply connected to the electrodes.

A power adjustment element may be also included to adjust the amount of electric power and to display the amount of the adjusted power.

The lateral flow assay strip may be switched from (i) the first state which does not form the flow path of the analytes between the sample pad and the test pad to (ii) the second state that forms the flow path of the analytes between the sample pad and the test pad.

The lateral flow assay strip may further comprise a state switching element for switching the state from the first state to the second state, and the state switching element may be operated in the manner of push, slide, turn, seesaw, removal of a barrier, or a combination thereof.

The state switching element may separate the preconcentration kit from the sample pad.

A conjugate pad may be further included, which is connected to the test pad and comprise an assembly in which detectors that bind to the analytes to produce conjugates are joined to indicators.

The conjugate pad and the state switching element may be configured in an integral body.

The test pad may comprise (i) a detection region containing the first captor for capturing the conjugates and/or (ii) a control region containing the second captor for capturing the assembly or detectors that failed to form the conjugates.

In another aspect of the present invention, a lateral flow assay strip is provided for detecting analytes in a sample, the lateral flow assay strip comprising: a support; a sample pad connected to the support and receiving the sample; a test pad connected to the support and comprising a captor for capturing the analytes; a case accommodating the lateral flow assay strip; and a state switching element for blocking or connecting the flow path of the analytes between the sample pad and the test pad, which is connected to the support, the sample pad, the test pad, or the case.

Effects of the Invention

As described above, the embodiments of the present invention have the effects that permit the detection of biomarkers at a low concentration by injecting samples into a sample pad, preconcentrating analytes by attaching a preconcentration kit to the sample pad, and transferring the analytes to a conjugate pad by connecting a conjugate pad to the sample pad.

Although not explicitly stated herein, the effects that are predictable from the technical feature of the present invention in the following description, drawings, examples, and claims and the potential effects resulting therefrom are regarded as those set forth in the specification of the present invention.

DETAILED DESCRIPTION OF THE INVENTION

In the following description of the present invention, a full explanation for related known functions is omitted when it is obvious to a person of ordinary skill in the art and deemed to unnecessarily blur the subject matter of the present invention. Some embodiments of the present invention are described in detail using the illustrative drawings.

Figure 1A:
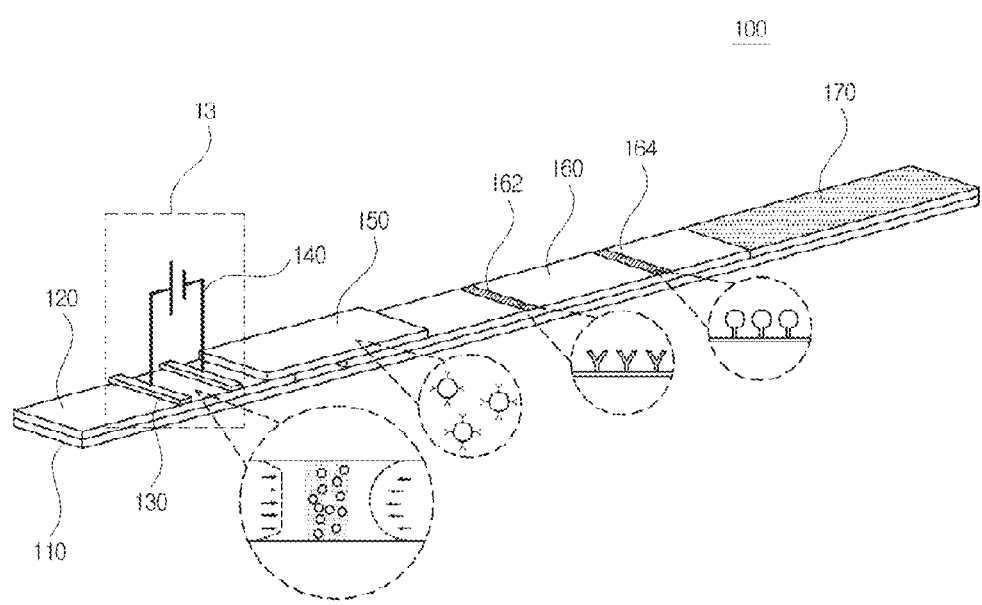
FIG. 1a is a drawing that illustrates a lateral flow assay strip according to one embodiment of the present invention.

FIG. 1a is a drawing that illustrates a lateral flow assay strip according to one embodiment of the present invention. Referring to FIG. 1a, the lateral flow assay strip (100) includes a sample pad (120), a preconcentration kit (13), a conjugate pad (150), a test pad (160), and an absorption pad (170).

The sample pad (120), the test pad (160), and the absorption pad (170) may be anchored to a support (110), and the test pad (160) may act as the support (110). The sample pad (120) is a pad into which samples to be detected are injected. The conjugate pad (150) is a pad containing a detector combined with color-developing materials. The detector binds to the analytes within the sample. The test pad (160)

comprises a detection region (162) and a control region (164), and displays whether the analytes exist within the sample and whether the sample is transferred. The absorption pad (170) is a pad that absorbs the sample using a capillary action. Pads can be implemented as porous media that respond to the capillary action. The medium includes, but is not limited to, cellulose, nitrocellulose, polyethersulfone, polyvinylidene, fluoride, nylon, and polytetrafluoroethylene that can be used for the lateral flow. The medium may be used alone or in combination with other substances.

The lateral flow assay strip (100) includes a preconcentration kit (13) for preconcentrating biomarkers at a low concentration. The preconcentration kit (13) includes a selective ion permeable membrane (130) and a power supply (140). The selective ion permeable membrane for preconcentrating samples can be implemented as Nafion, polystyrene sulfonate (PSS), or polyallylamine hydrochloride (PAH).

The selective ion permeable membrane (130) is connected to a power supply. The selective ion permeable membrane (130) may be equipped with thin film electrodes so that it can be connected to external power supplies. In the dual selective ion permeable membrane (130), a cathode, an anode, or a ground is connected through a wire, resulting in a potential difference at both ends.

The selective ion permeable membrane (130) may be patterned on the sample pad (110) or attached to the sample pad (110) with adhesive tapes or the like. The sample pad (110) acts as a channel. The channel on which the selective ion permeable membrane is patterned functions as a sort of nanofilter which selectively penetrates protons. For example, in case where the selective ion permeable membrane is Nafion, SO3- in the chemical structure of Nafion allows H+ ions to be penetrated selectively and rapidly by hopping and vehicle mechanisms. Therefore, protein materials to be analyzed can be efficiently preconcentrated in certain regions of the channel in a very fast time via the selective ion permeable materials such as Nafion.

The preconcentrated kit may be implemented to generate ICP (ion concentration polarization) phenomena by using microporous materials (e.g., hydrogel, etc.). It may be implemented as microporous permeable membranes made of natural or artificial materials. In such a case, micropores may have the pore diameter >10 nm and the pore volume >0.6 mL/g; however, this is exemplary and illustrative only, not limiting in scope. Micropores with an appropriate size can be used depending on the designs embodied.

Microporous materials (e.g., nafion, etc.) are infiltrated into the sample pad. The preconcentration kit may be produced by means of infiltrating microporous materials in liquid form into a permeable membrane (e.g., paper, etc.) and drying them.

Figure 1B:
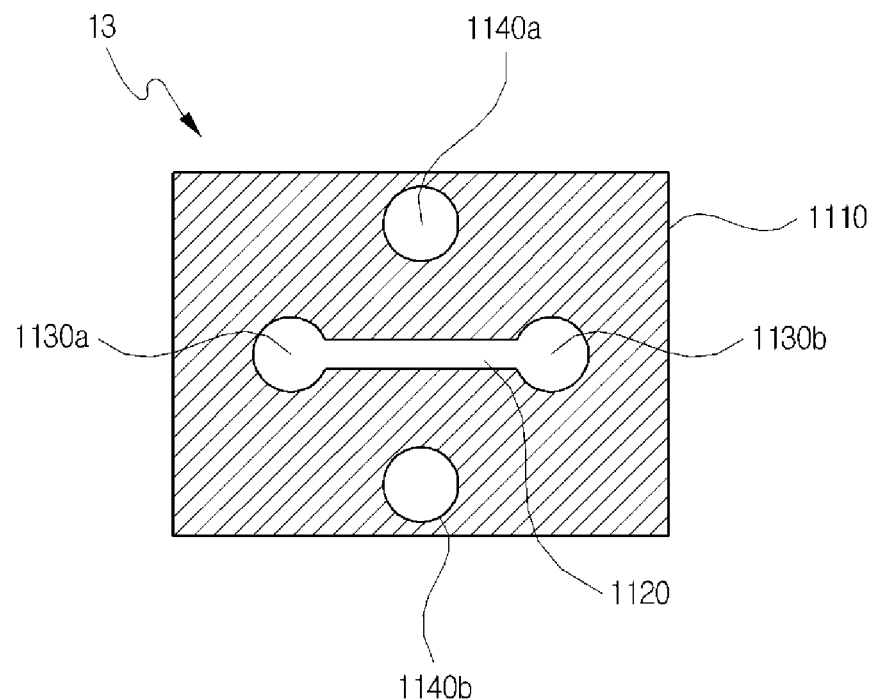
FIGS. 1b to 1e are the drawings that illustrate a preconcentration kit of a lateral flow assay strip according to one embodiment of the present invention.
Figure 1C:
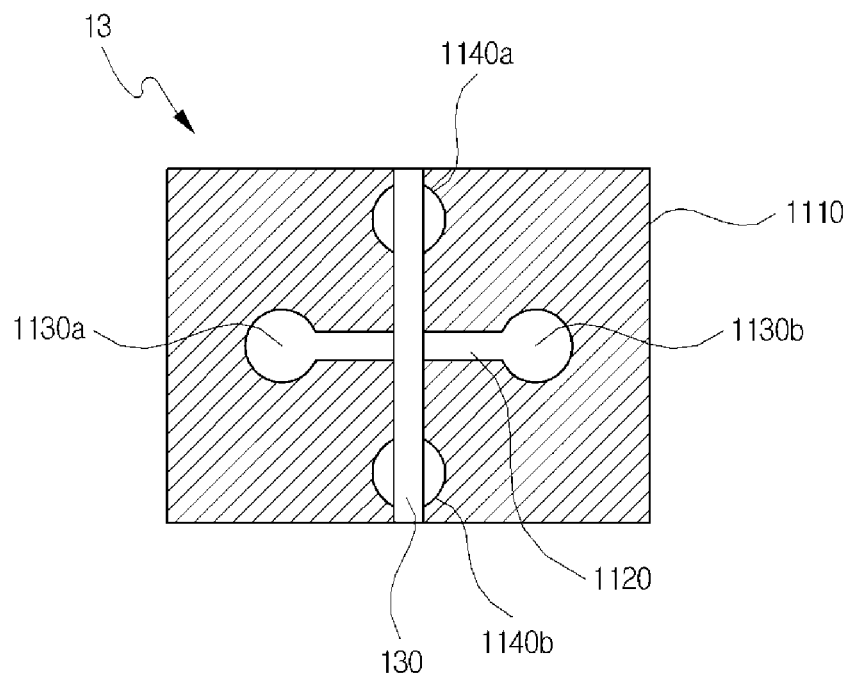
Figure 1D:
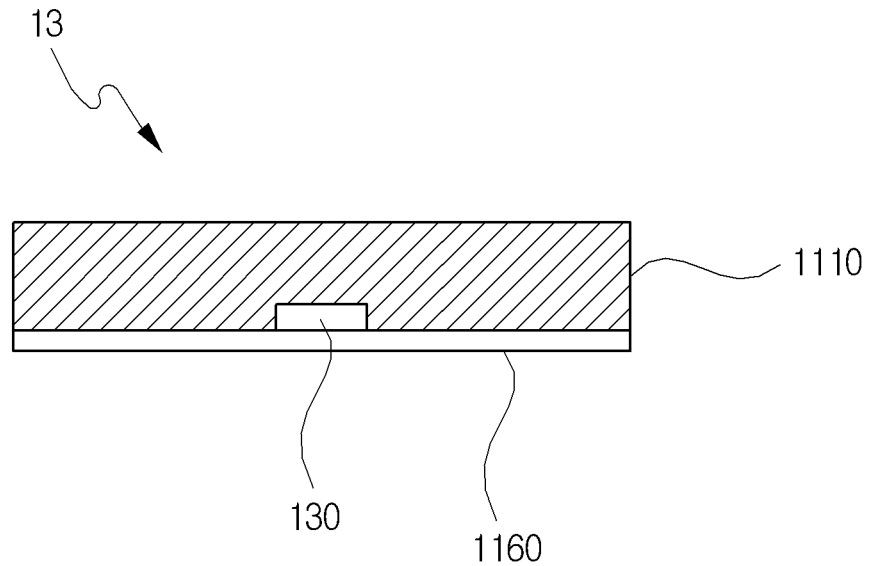

Referring to FIGS. 1b to 1e, a preconcentrated kit comprising a single selective ion permeable membrane is illustrated. A single selective ion permeable membrane can allow to employ ICP using a depletion force arising from the single selective ion permeable membrane and the flow of the fluid from the sample pad to the absorption pad. Referring to FIGS. 1b to 1d, the preconcentration kit according to one embodiment of the present invention includes a paper (1110) and a selective ion permeable membrane (130). Papers (1110) are composed of materials that are able to absorb water well (hydrophilic materials). However, if hydrophobic materials are infiltrated into a portion of the paper (1110), that portion fails to absorb water.

Channels (1120) and buffers (1140a, 1140b) are formed by infiltrating hydrophobic materials into the paper (1110). The hydrophobic materials may surround the channels (1120) and the buffers (1140a, 1140b) to form the channels (130) and the buffers (1140a, 1140b). That is, hydrophobic materials do not infiltrate into the regions of the channels (1120) and the buffers (1140a, 1140b), which are kept hydrophilic. It is the regions surrounding the channels (1120) and the buffers (1140a, 1140b) that hydrophobic materials do infiltrate into and which become hydrophobic. Thus, if water (or other solutions) drops on the channels (1120) or the buffers (1140a, 1140b), the water can only spread within the regions without escaping from the channels (1120) or the buffers (1140a, 1140b). Hydrophobic materials may be any materials that are hydrophobic; for example, the hydrophobic materials may be wax. For the convenience of explanation, the following describes the case where wax infiltrated into the paper (1110) to form channels (1120) and buffers (1140a, 1140b).

Channels (1120), which are produced in the form of a long hydrophilic line, act as a capillary in the preconcentration kit (13). At least one of the two ends (1130a, 1130b) of the channel (1120) may have the wider width than the middle part of the channel (1120). Since liquid drops on one end of the channel (1130a, 1130b) for the preconcentration, securing a sufficiently wide width can make the preconcentration work much easier. Also, the opposite end (1130a, 1130b) should be wide enough to mitigate the ionic polarization phenomenon to some extent as described below and to enhance the effect of an extraction pad.

Buffers (1140a, 1140b) are formed apart from the channels. Buffers in any shapes are permissible. They are only required to be formed in a proper size for the preconcentration work by dropping water on the buffers. In the embodiments of the present invention, the shape of the buffers is illustrated in a circular form, but any different shapes are acceptable. In the embodiments of the present invention, there are two discrete buffers, but only one may be formed.

The selective ion permeable membrane (130) is formed to connect with the buffers (1140a, 1140b) and intersect with the channels (1120). The selective ion permeable membrane (130) includes nanochannels (nanoporous membranes) made up of selective ion permeable materials that selectively pass ions. Selective ion permeable materials refer to the materials that bind well to a particular ion with both being attracted to each other, but do not bind well to the other ions without attracting them. Selective ion permeable materials may be, for example, Nafion. For the convenience of explanation, the following describes the case where Nafion was used as a selective ion permeable material, i.e., the selective ion permeable membrane (130) was a Nafion line.

The selective ion permeable membrane (130) may be formed, for example, to connect the two buffers (1140a, 1140b) and intersect with the channels (1120).

The selective ion permeable membrane (130) is formed on one side of the paper (1110). When it is used for the preconcentration, the selective ion permeable membrane (130) may be located at the bottom of the paper.

The preconcentration kit (13) may further comprise a single-sided adhesive tape (1160). The single-sided adhesive tape (1160) is a component for holding the paper (1110) and the selective ion permeable membrane (130) by combining them together. Any adhesive members other than a single-sided adhesive tape (1160) may be used.

The preconcentration kit (13) may contain additional extraction pads attached to one end (1130b) of the channel (1120). The extraction pad attached to one end (1130b) of the channel (1120) extracts the substances of the analytes that have passed through the selective ion permeable membrane (130) outside of the channel (1120). This allows the substances of being analyzed to be continuously passed through the selective ion permeable membrane (130), thereby making it possible to preconcentrate the substances to be preconcentrated at a higher concentration.

Figure 1E:
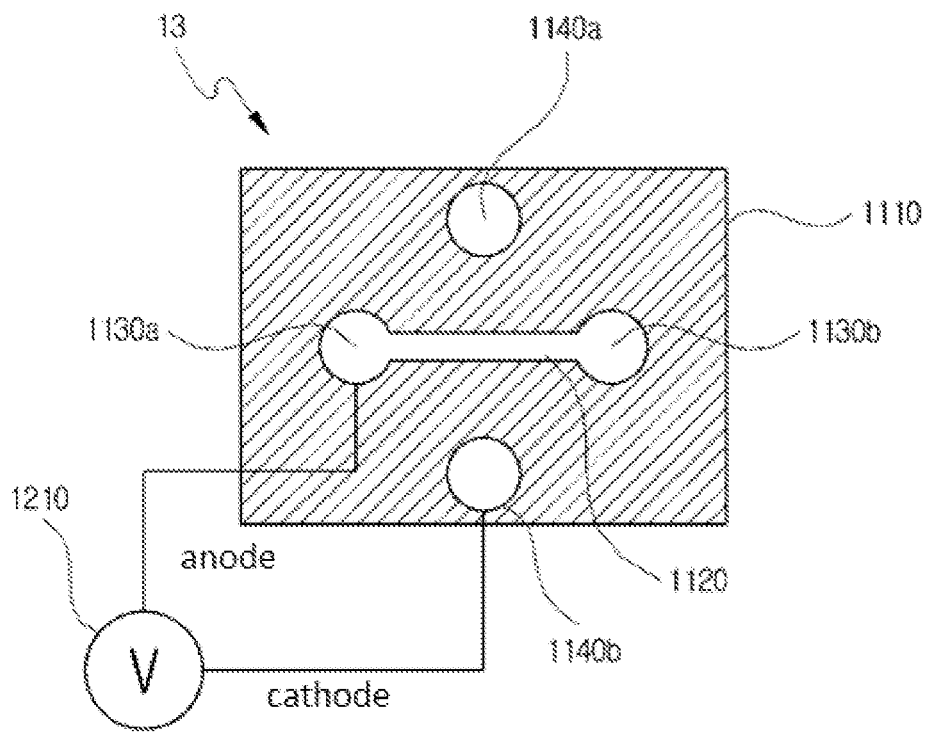

FIG. 1e illustrates a preconcentration kit (13) with a power supply (1210).

Referring to FIG. 1e, an anode of the power supply (1210) is connected to one end (1130a) of the channel (1120) and a cathode is connected to one of the buffers (1140b). When a voltage is applied by the power supply (1210), the preconcentration may proceed as described below. If the electric power is omitted, gravity, magnetic fields, or other catalysts may be used to diffuse ions instead of voltages.

It is assumed that a manufacturing process is carried out by a manufacturing device.

The manufacturing device adsorbs hydrophobic materials onto a paper. For example, the manufacturing device may adsorb hydrophobic materials onto a paper by printing wax on the paper. In the embodiments of the present invention, as shown in FIG. 1a, the manufacturing device may adsorb hydrophobic materials onto a paper according to the patterns of the channels and the buffers in the manner of printing wax on the regions other than the channels (1120) and the buffers (1140a, 1140b) (the regions forming the boundary of the channels (1120) and the boundary of the buffers (1140a, 1140b)). Wax may be printed on a paper depending on the shapes of the channels (1120) and the buffers (1140a, 1140b) by using wax printers and general-purpose computers.

Channels (1120) are produced in the form of a long line to act as a capillary in the preconcentration kit (13). At least one of the two ends (1130a, 1130b) of the channel (1120) may have the wider width than the middle part of the channel (1120). Since liquid drops on both ends (1130a, 1130b) of the channel (1120) for the preconcentration, securing a sufficiently wide width can make the preconcentration work much easier.

Buffers (1140a, 1140b) are formed apart from the channels. Buffers in any shapes are permissible. They are only required to be formed in a proper size for the preconcentration work by dropping water on the buffers. In the embodiments of the present invention, the shape of the buffers is illustrated in a circular form, but any different shapes are acceptable. In the embodiments of the present invention, there are two discrete buffers, but only one may be formed.

The manufacturing device infiltrates hydrophobic materials into a paper. For example, the manufacturing device may infiltrate wax into a paper by heating up a paper on which wax is printed. When a paper with wax printed is heated for two minutes at 130° C. on a hot plate, the wax printed on the paper becomes melted or in the state that can permeate the paper, thereby infiltrating into the paper. Accordingly, the regions of the paper other than the channels (1120) and the buffers (1140a, 1140b) are infiltrated by hydrophobic wax, and thus water is unable to diffuse within said regions and only permitted to diffuse in the regions of the channels (1120) and the buffers (1140a, 1140b) (which become hydrophilic).

The regions of the channels (1120) and the buffers (1140a, 1140b) are made of paper and remain hydrophilic since they have not been infiltrated by hydrophobic materials. However, hydrophobic materials (e.g., wax) infiltrate the regions of the paper surrounding the channels (1120) and the buffers (1140a, 1140b), thereby forming the channels (1120) and the buffers (1140a, 1140b). The regions surrounding the channels (1120) and buffers (1140a, 1140b) are hydrophobic due to the infiltration of hydrophobic materials (e.g., wax).

The manufacturing device produces a selective ion permeable membrane (130) as illustrated in FIG. 1c on one side of the paper.

The selective ion permeable membrane (130) is formed to connect with the buffers (1140a, 1140b) and intersect with the channels (1120). The selective ion permeable membrane (130) includes nanochannels (nanoporous membranes) made up of selective ion permeable materials that selectively pass ions. Selective ion permeable materials refer to the materials that bind well to a particular ion with both being attracted to each other, but do not bind well to the other ions without attracting them. Selective ion permeable materials may be, for example, Nafion. For the convenience of explanation, the following describes the case where Nafion was used as a selective ion permeable material, i.e., the selective ion permeable membrane (130) was a Nafion line.

The selective ion permeable membrane (130) may be formed, for example, to connect the two buffers (1140a, 1140b) and intersect with the channels (1120). The selective ion permeable membrane (130) is formed on one side of the paper (1110). When it is used for the preconcentration, the selective ion permeable membrane (130) may be located at the bottom of the paper.

The manufacturing device connects a power supply to the paper (1110). As depicted in FIG. 1e, an anode of the power supply (1210) is connected to one end (1130a) of the channel (1120) and a cathode is connected to one of the buffers (1140b). When a voltage is applied by the electric power (1210), the preconcentration may proceed as described below.

In a modified embodiment of the present invention, a manufacturing device may attach extraction pads to one end (1130b) of the channel (1120). The extraction pad attached to one end (1130b) of the channel (1120) extracts the substances of the analytes that have passed through the selective ion permeable membrane (130) outside of the channel (1120). This allows the substances of being analyzed to be continuously passed through the selective ion permeable membrane (130), thereby making it possible to preconcentrate the substances to be preconcentrated at a higher concentration.

The sample pad, i.e., the channel, may also be implemented as porous membranes prepared by other kinds of materials that can provide passive capillary force. In addition, the following examples illustrate the case where the number of the patterned selective ion permeable membranes (130) is two, but it is noted that in some cases more may be patterned and attached on a straight line.

If a voltage difference occurs by applying the electric power to the selective ion permeable membranes (130) placed on both ends, ions of the fluid are forced to be attracted to the electrodes with opposite electrical properties to each ion due to the electric field resulting from the voltage difference. As the ions flow within the channels according to their electrical properties, they also take the fluid particles together due to the viscous forces. Thus, the overall flow of the fluid is generated. This flow of the fluid is referred to as Electro-Osmosis Flow (EOF) and the flow of the ions is referred to as electrophoresis (EP).

The capillary electrophoresis and the electro-osmosis vary in the vicinity of the channels implemented as selective ion permeable membranes, eliciting ion concentration polarization (ICP). Therefore, the reaction regions of the channels toward the cathode are subjected to ion depletion, but those toward the anode are subjected to ion enrichment. Then, the depleted, low ion concentration and the resulting high electric field allow the Depletion Zone to act as an electric barrier to the charged analytes. As a result, the analytes fail to pass through the Depletion Zone and are concentrated ahead of it. The analytes are concentrated in a very fast time in front of the Depletion Zone within the channels. Since the size of the Depletion Zone caused by the ion concentration polarization are extending as the ion concentration polarization of the samples proceed, the analytes make a preconcentrated zone in the middle part of the channels.

The lateral flow assay method is not limited to antibody-antigen reactions. The binding sites (ligands) mentioned in the specification of the present invention comprise protein ligands, binding sites in the sequences of nucleic acid molecules (DNA or RNA) or the like in various analytes, and specific binding materials comprise, but are not limited to, all biomolecules that are capable of selectively and specifically binding to the binding sites, including proteins, virus, phages, nucleic acid molecules Aptamer, and Hapten (DNP).

Figure 2A:
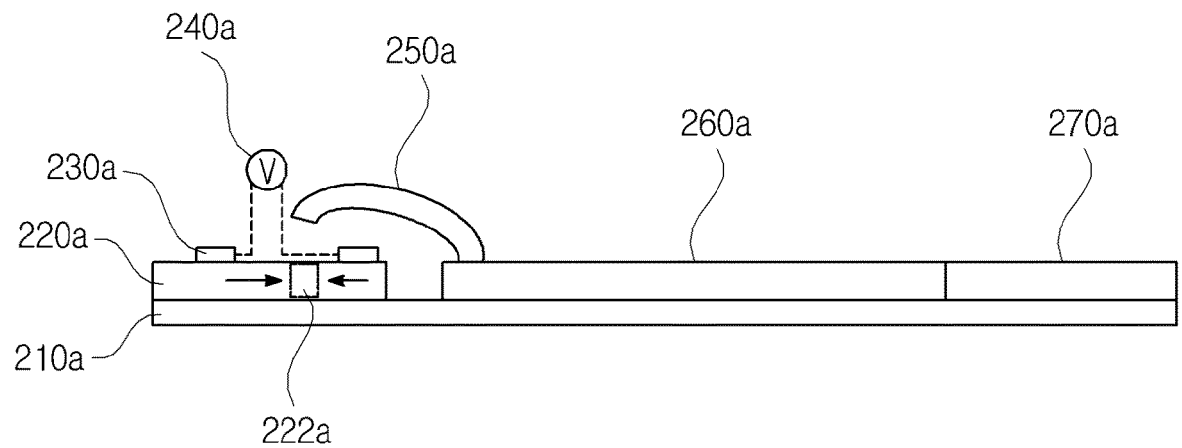
FIGS. 2a to 2g are the drawings that illustrate various lateral flow assay strips according to the embodiments of the present invention.
Figure 2B:
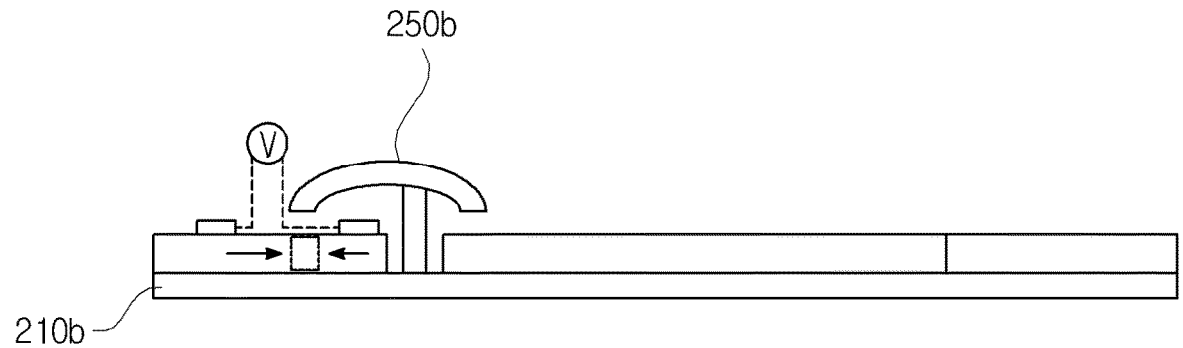
Figure 2C:
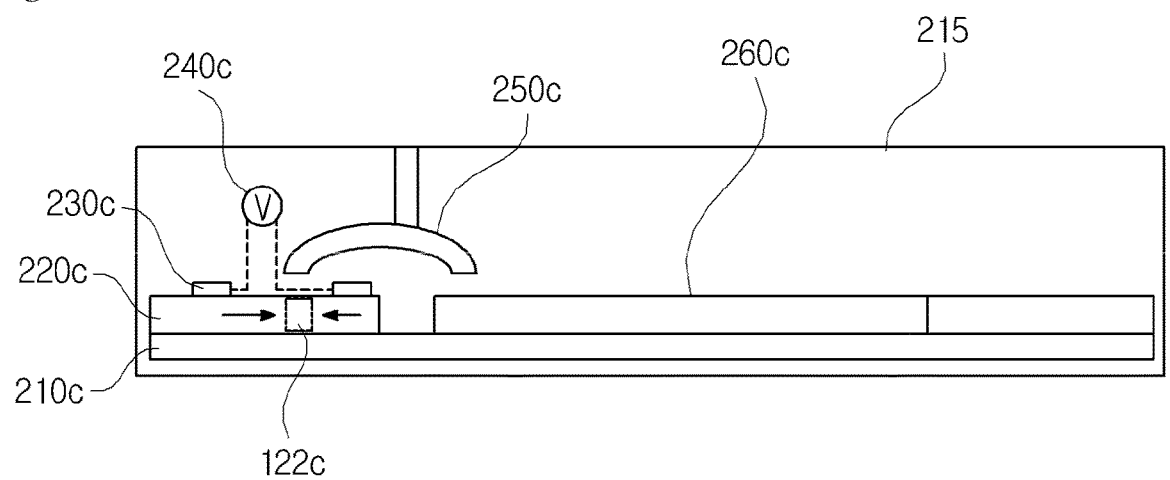

Below is the description of a bridge pad which is separated from the sample pad. In FIGS. 2a to 2c, bridge pads separated from the sample pad are illustrated.

Referring to FIG. 2a, the lateral flow assay strip for detecting the analytes in a sample includes a support ($210a$), a sample pad ($220a$), a bridge pad ($250a$), and a test pad ($260a$). The lateral flow assay strip may omit some of the various components illustrated in FIG. 1 or may include additional components.

The sample pad ($220a$) is connected to the support ($210a$) and receives samples.

The sample pad ($220a$) comprises a preconcentration kit, and the preconcentration kit comprises a selective ion permeable membrane ($230a$) and electrodes connected to the selective ion permeable membrane ($230a$). When the electric power is applied to the selective ion permeable membrane ($230a$), the preconcentrated zone ($222a$) is formed in the middle of the sample pad ($220a$).

The test pad ($260a$) is connected to the support ($210a$) and includes a captor for capturing the analytes.

The absorption pad ($270a$) is connected to the test pad ($260a$) and absorbs a sample by a capillary action. Depending on the shape, materials, etc. of the absorption pad ($270a$), the flow rate of the sample varies. The absorption pad ($270a$) is manufactured with its length or absorption capacity adjusted.

The bridge pad ($250a$) is formed apart from the sample pad ($220a$) by a specified distance to avoid contacting with the sample pad ($220a$). Referring to FIG. 2a, the bridge pad ($250a$) may be connected to the test pad ($260a$). Referring to FIG. 2b, the bridge pad ($250b$) may be connected to the support ($210b$).

Referring to FIG. 2c, the lateral flow assay strip for detecting the analytes in a sample includes a support ($210c$), a sample pad ($220c$), a bridge pad ($250c$), a test pad ($260c$), and a case ($215$).

The case ($215$) is formed to accommodate the lateral flow assay strip.

Bridge pads ($250c$) are formed apart from the sample pad ($220c$) by a specified distance. The bridge pad ($250c$) may be connected to the case ($215$).

Bridge pads ($250c$) may be attached to the case ($215$) or the like and the attachment is not limited to any particular method. For example, if a bridge pad ($250c$) is attached to a case ($215$) and pressure is applied to the case ($215$), the bridge pad ($250c$) may be manufactured so that it can be in contact with the lateral flow assay strip.

The following describes a bridge pad in contact with the sample pad. FIGS. 2d to 2g illustrate the bridge pad in contact with the sample pad.

Figure 2D:
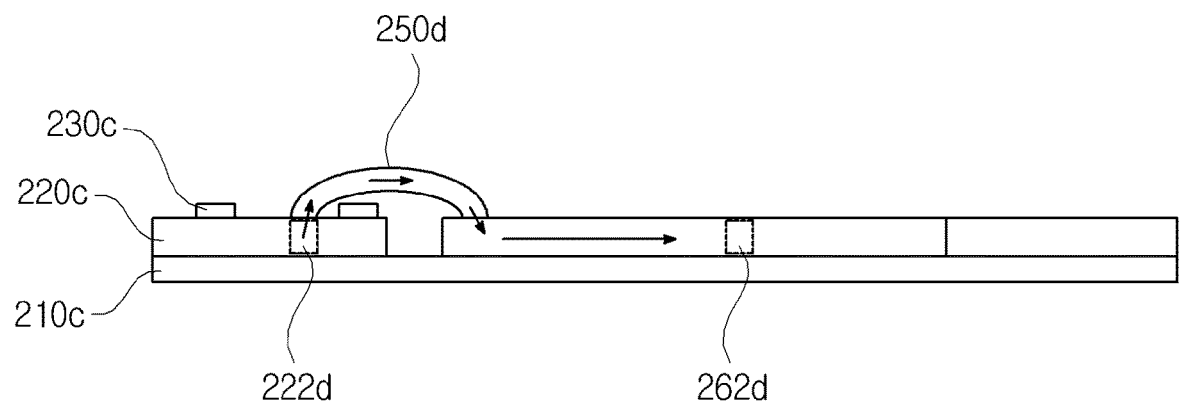

Referring to FIG. 2d, the bridge pad ($250d$) is switched from the first state to the second state. The first state refers to the state where the bridge pad is not in contact with the sample pad, and the second state indicates the state where the bridge pad is in contact with the sample pad, forming a flow path of the analytes between the sample pad ($220c$) and the test pad ($260d$). The bridge pad ($250d$) may be in contact with the preconcentrated zone ($222d$) of the sample pad ($220c$). The preconcentrated analytes flow through the bridge pad ($250d$) to the test pad ($260d$).

The test pad ($260a$) is connected to the support ($210a$) and comprises a captor ($262d$) for capturing the preconcentrated analytes.

Figure 2E:
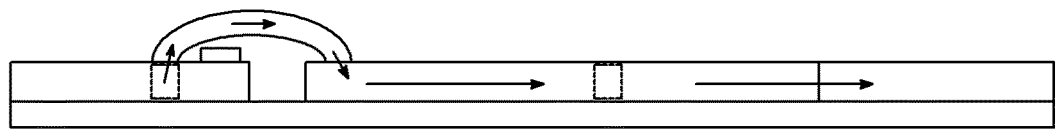

Before the transition from the first state of the bridge pad ($250d$) to the second state, electrodes ($230d$) may be removed from the sample pad ($220c$). This is illustrated in FIG. 2e.

Figure 2F:
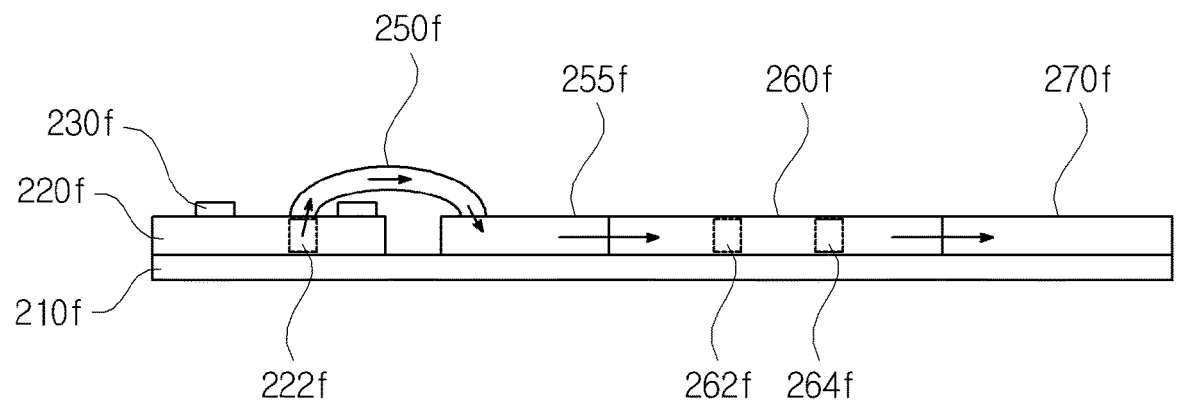

Referring to FIG. 2f, the lateral flow assay strip includes a conjugate pad ($255f$).

The conjugate pad ($255f$) is connected to the test pad ($260f$) and comprises an assembly in which detectors that bind to the analytes to produce conjugates are joined to indicators.

Indicators are substances that generate a signal so that they can be detected with the naked eyes or a sensor. Indicators may be, but not limited to, color-developing materials, for example, gold nanoparticles, and any appropriate materials are acceptable depending on the designs embodied.

Figure 2G:
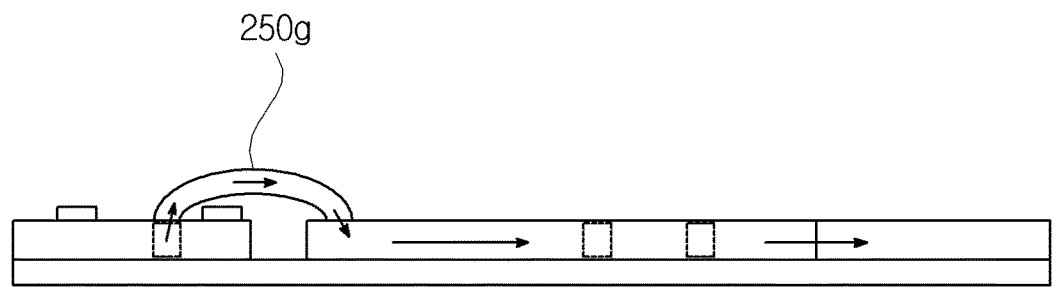

The conjugate pad ($255f$) and the bridge pad ($250f$) may be configured in an integral body, which is illustrated in FIG. 2g.

The test pad ($260f$) comprises at least one of a detection region ($262f$) and a control region ($264f$). The detection region ($262f$) comprises the first captor for capturing the conjugates. In other words, the detection region ($262f$) determines whether the sample contains the analytes. The control region ($264f$) comprises the second captor for capturing the assembly or detectors that failed to form the conjugates. Thus, the control region ($264f$) confirms whether the sample has flowed, regardless of whether the analytes exist or not.

A reaction that produces conjugates in the conjugate pad ($255f$) or captures them in the test pad ($260f$) may be a physical reaction, a chemical reaction, a biological reaction, or the combination thereof. For example, it may be an antigen-antibody reaction.

In the conjugate pad ($255f$), the indicator-detector assembly is located, and the analytes pass through the conjugate pad ($255f$), producing the indicator-detector-analyte conjugates. The indicator-detector-analyte conjugates flowed are captured by the first captor in the detection region ($262f$).

The lateral flow assay strip further comprises a state switching element for switching the bridge pad from the first state to the second state. FIGS. 3a to 3c, 4a to 4c, and 5a to 5d are the drawings that illustrate the state switching elements of the lateral flow assay strip according to the embodiments of the present invention.

The state switching element is provided with the structure by which it removes the conjugate pad when the analytes are preconcentrated, or connects the conjugate pad when the analytes are detected. The state switching element may remove the preconcentration kit from the sample pad. Alternatively, the state switching element may connect the preconcentration kit to the sample pad.

Figure 3A:
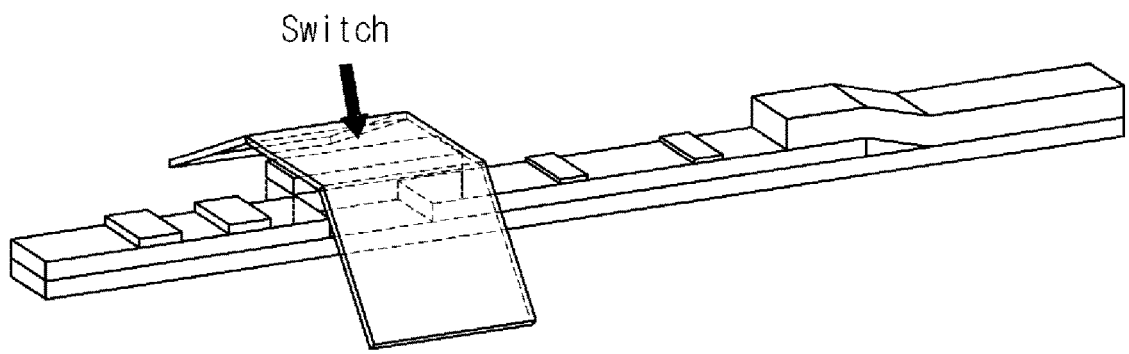
FIGS. 3a to 3c, 4a to 4c, and 5a to 5d are the drawings that illustrate a state switching element of a lateral flow assay strip according to the embodiments of the present invention.
Figure 3B:
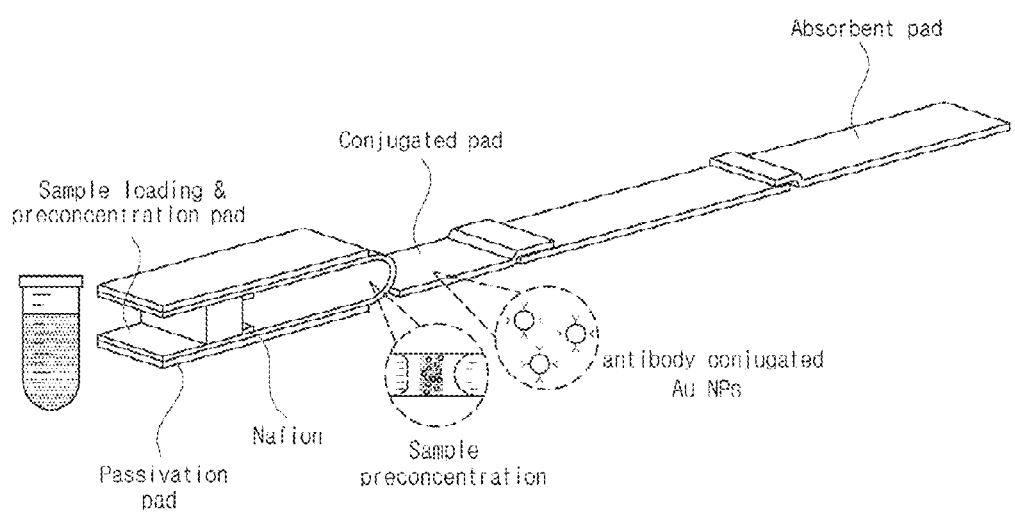
Figure 3C:
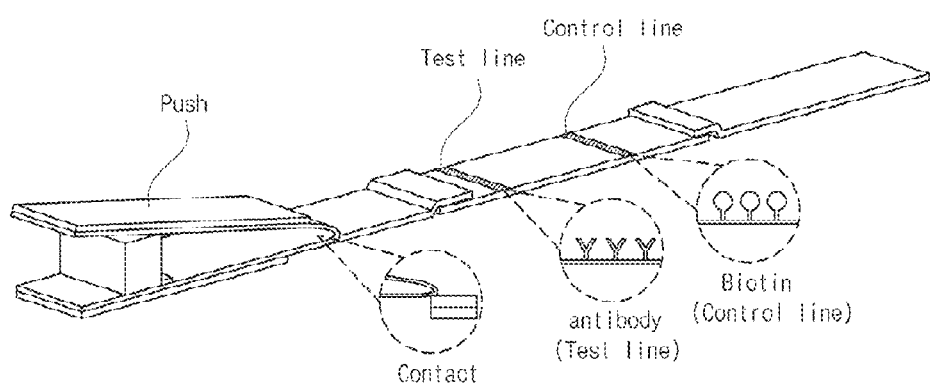
Figure 4A:
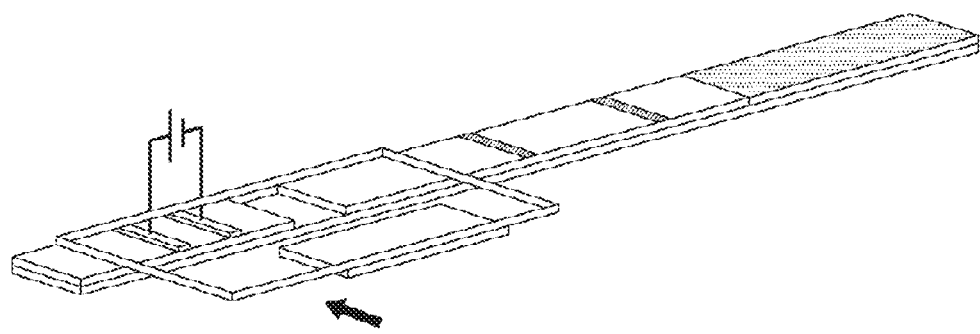
Figure 4B:
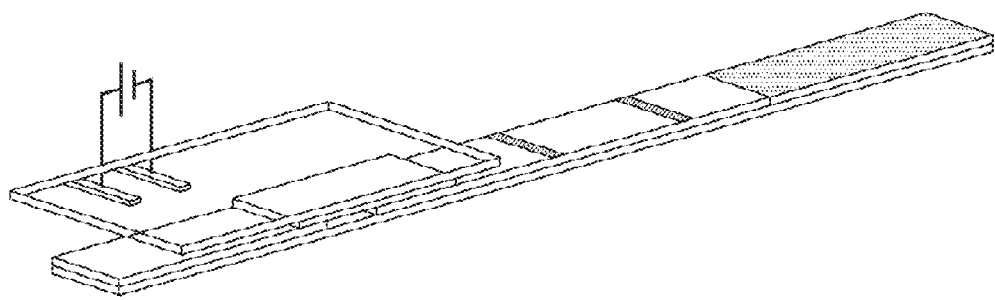
Figure 4C:
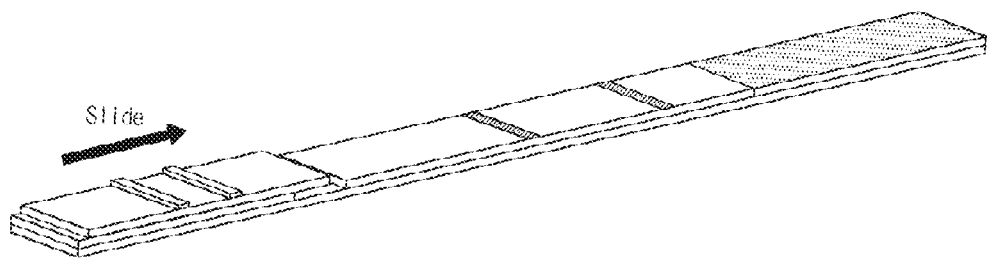
Figure 5A:
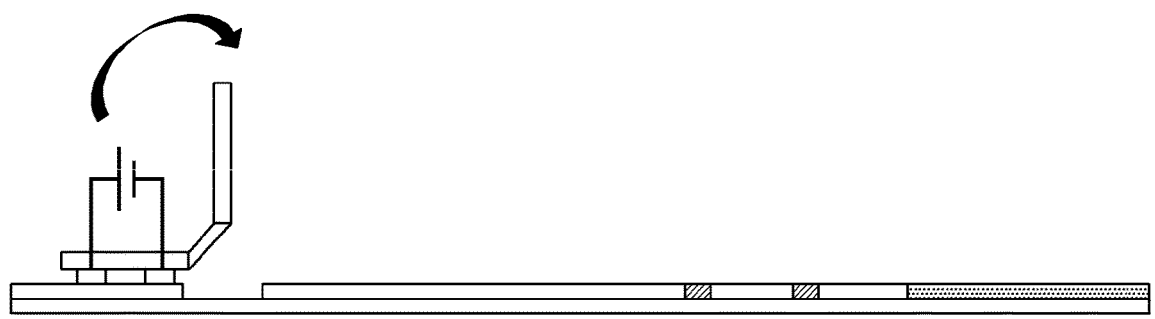
Figure 5B:
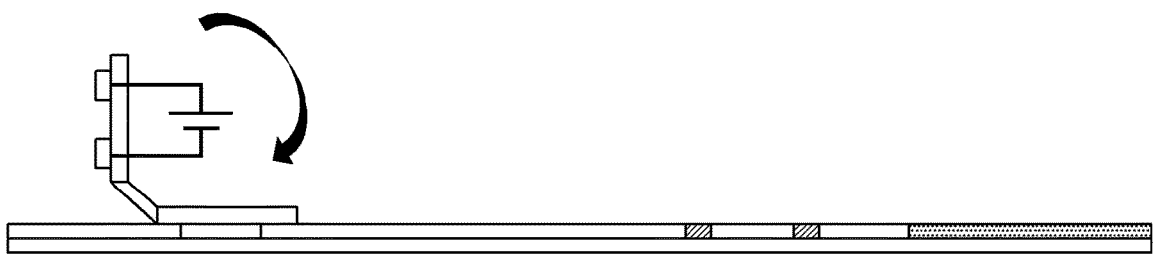
Figure 5C:
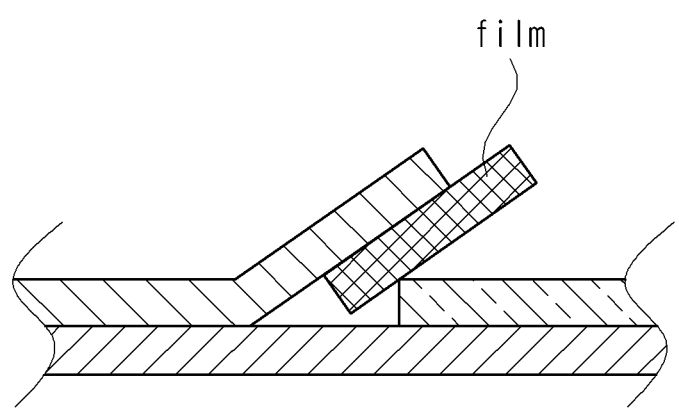
Figure 5D:
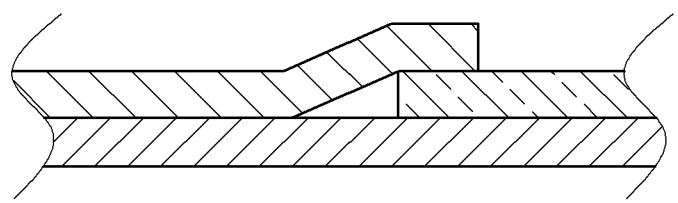

The state switching element is operated in the manner of push, slide, turn, seesaw, or the combination thereof. FIGS. 3a to 3c illustrate the state switching element which is operating in a push manner, FIGS. 4a to 4c exemplify the state switching element in a slide manner, FIGS. 5a to 5b shows the seesaw-type state switching element, and FIGS. 5c to 5d illustrate the state switching element which is operating by removing a barrier (e.g., OHP film, etc.).

The followings describe the experimental results according to the selective ion permeable membrane and the electrodes of the preconcentration kit in the lateral flow assay strip while referring to FIGS. 6 to 13.

The preconcentration kits comprise a selective ion permeable membrane and electrodes. The selective ion permeable membrane may exist in multiple numbers. The miltiple selective ion permeable membranes are separately located according to the flow direction of the lateral flow assay strip.

Figure 6A:
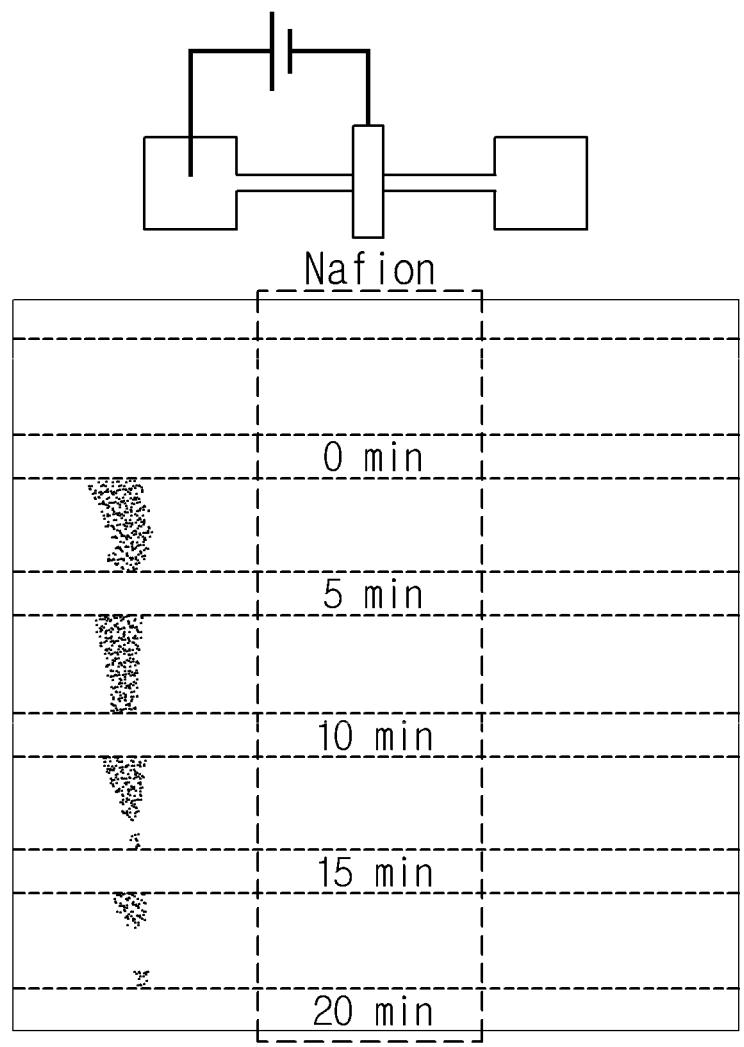
FIGS. 6a and 6b are the drawings that illustrate a single permeable membrane and a dual permeable membrane in a preconcentration kit for a lateral flow assay strip according to the embodiments of the present invention.
Figure 6B:
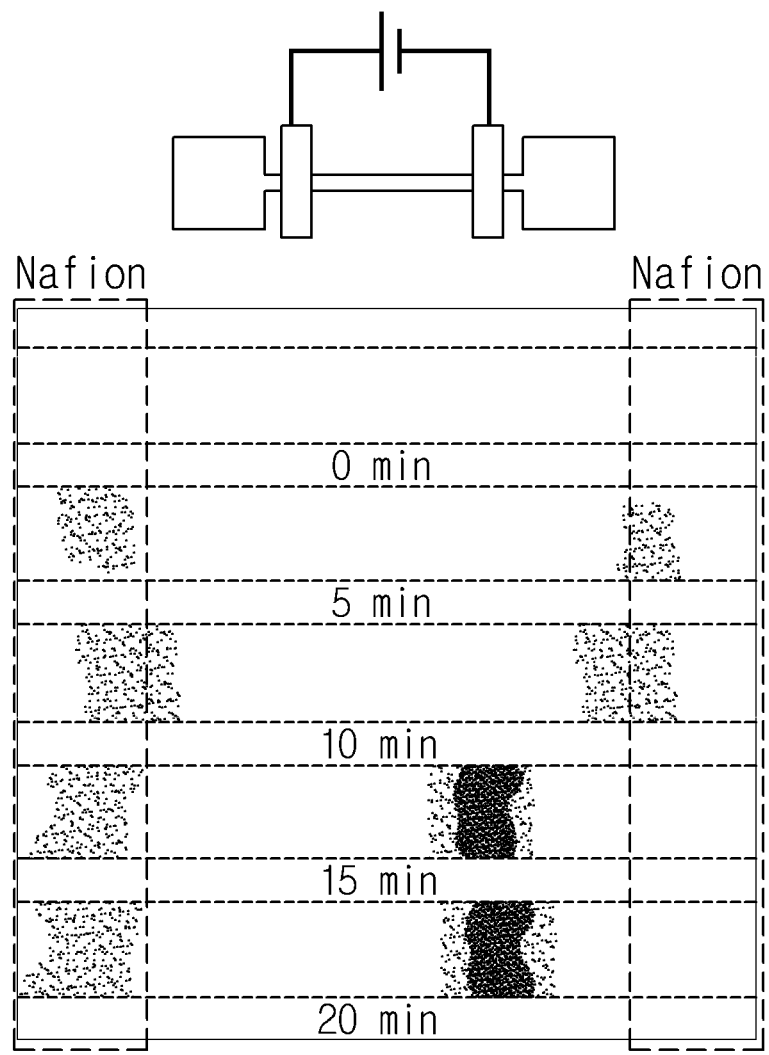
Figure 7:
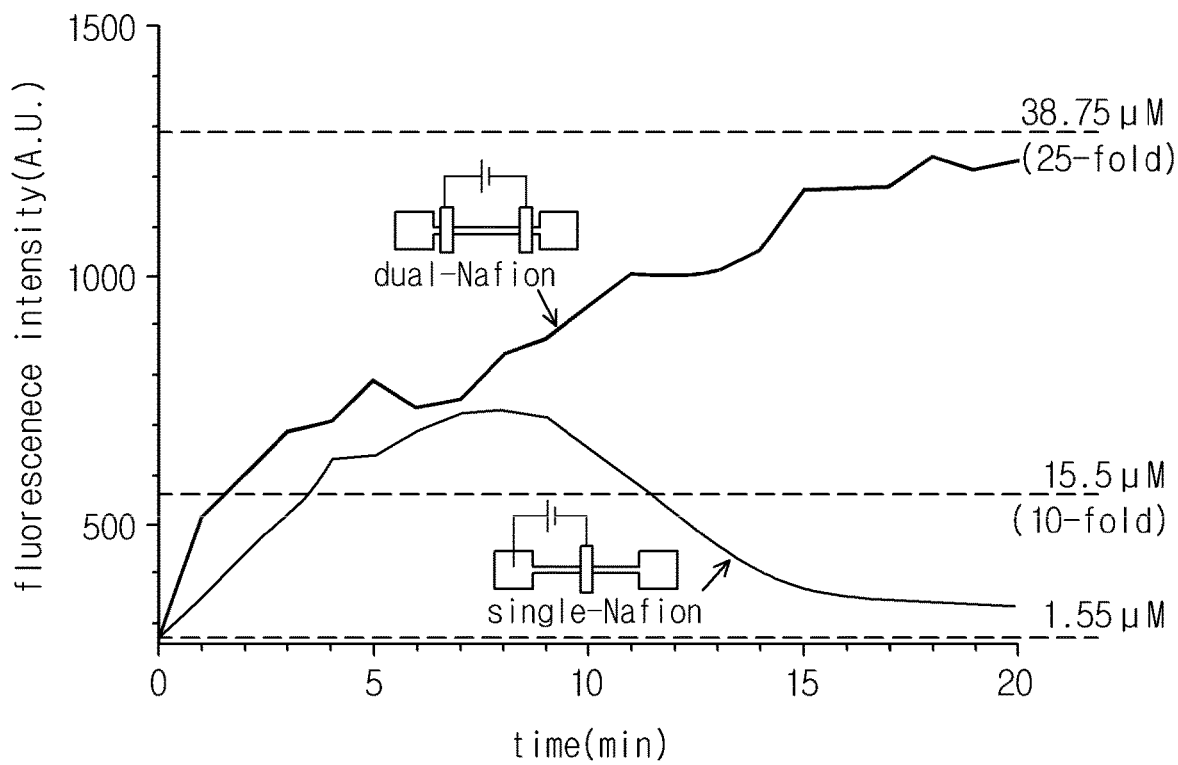
FIG. 7 is a drawing that illustrates fluorescence intensity in a single permeable membrane and a dual permeable membrane in a preconcentration kit for a lateral flow assay strip according to the embodiments of the present invention.

FIGS. 6a and 6b are the drawings that illustrate the preconcentrated analytes by a single permeable membrane and a dual permeable membrane in the preconcentration kit for the lateral flow analysis strip, and FIG. 7 is a drawing that illustrates fluorescence intensity by the single permeable membrane and the dual permeable membrane. Referring to FIGS. 6 and 7, it was readily noted that unlike the preconcentration kit using one permeable membrane, i.e., single nafion, the preconcentration kit using two permeable membranes, i.e., dual nafion, allowed the preconcentration to proceed even after a certain time lapses. For example, even after 8 minutes lapsed, the preconcentration kit using the dual nafion enabled to preconcentrate the analytes as much as a target value.

The preconcentration kit may further comprise a power supply connected to the electrodes. The lateral flow assay strip may further comprise a power adjustment element for adjusting the amount of the electric power and displaying the amount of the adjusted electric power.

Figure 8A:
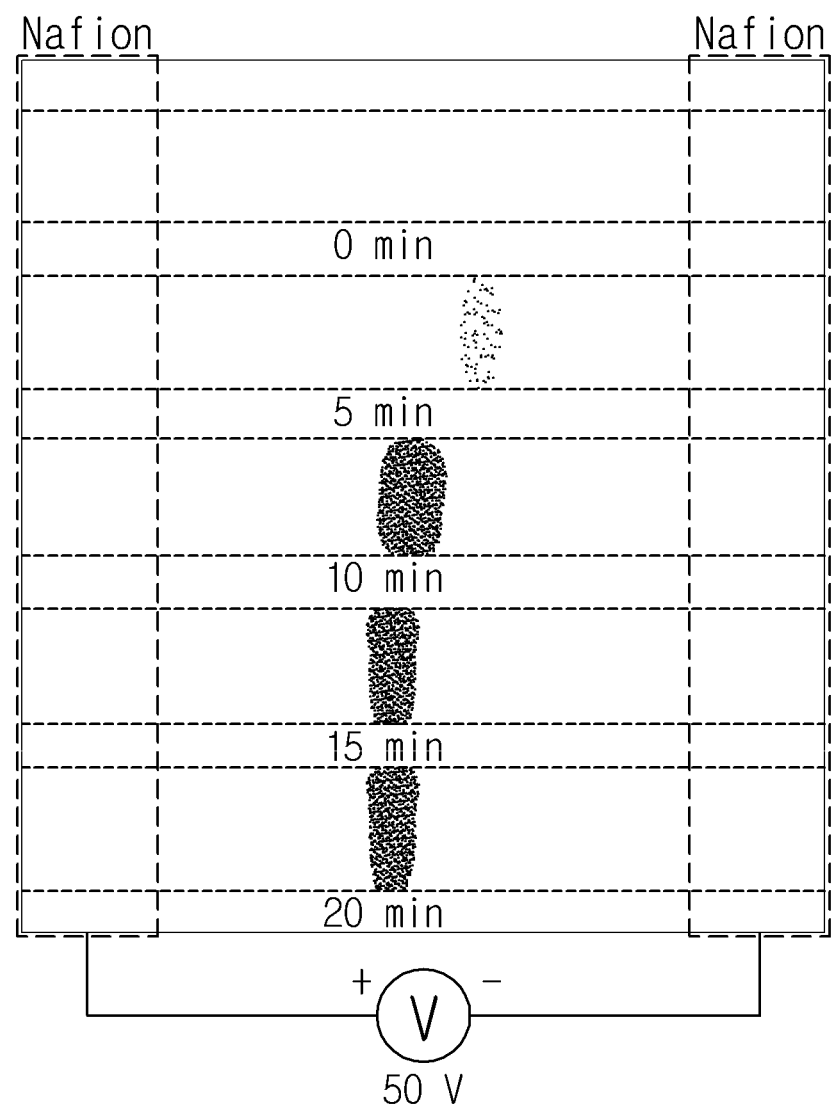
FIGS. 8a, 8b, and 9 are the drawings that illustrate the results from the preconcentration by applying different voltages to a preconcentration kit for a lateral flow assay strip according to one embodiment of the present invention.
Figure 8B:
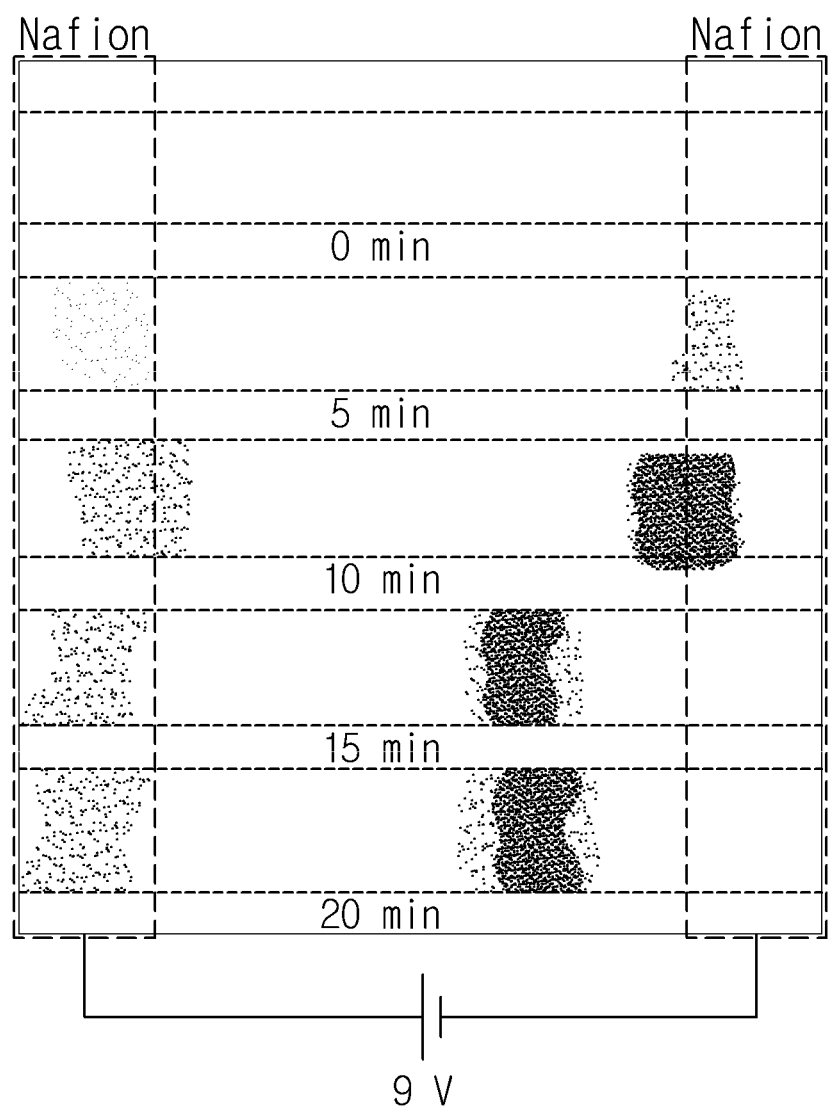
Figure 9:
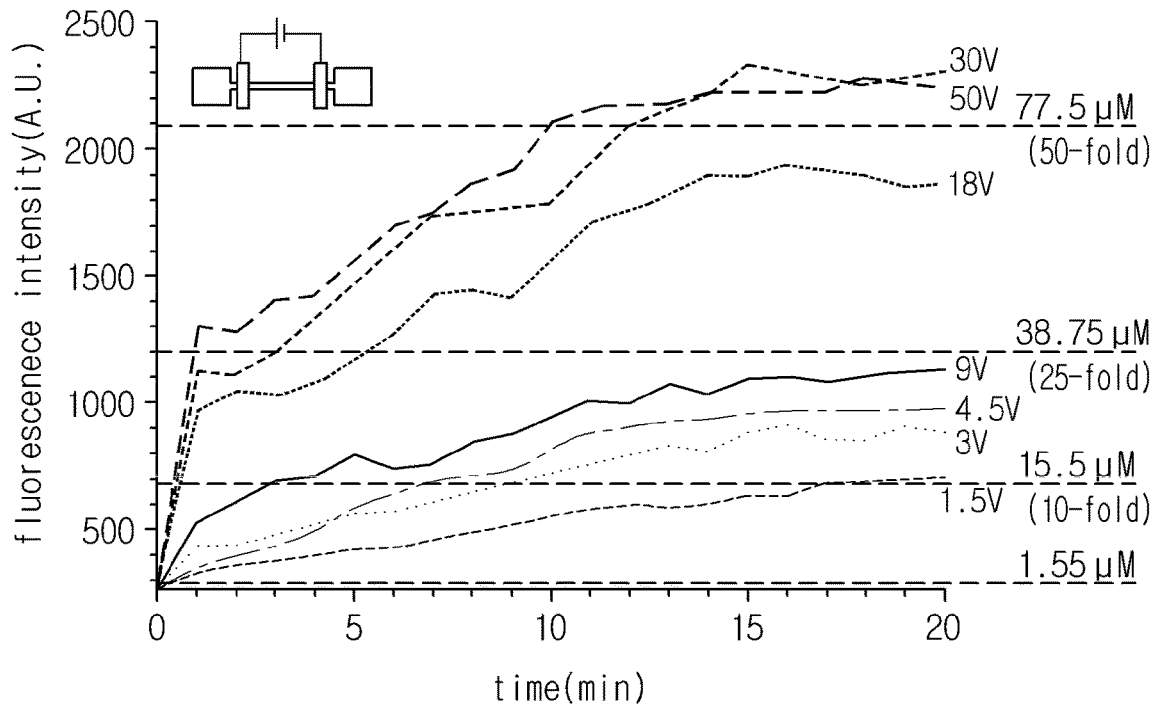

FIGS. 8a, 8b, and 9 are the drawings that illustrate the results of preconcentration by applying different voltages to the preconcentration kit for the lateral flow assay strip. Referring to FIGS. 8 and 9, it was easily understood that the preconcentration kit with high voltages allowed the higher concentration rate than that using low voltages, and that the amounts of the preconcentrated analytes did not increase any more above a certain voltage. For example, the amounts of preconcentration were similar between the preconcentration kit with 30 V and that using 50 V. Furthermore, the preconcentration kit using a commercial battery of 9 V was able to preconcentrate the analytes as much as the target value.

Figure 10:
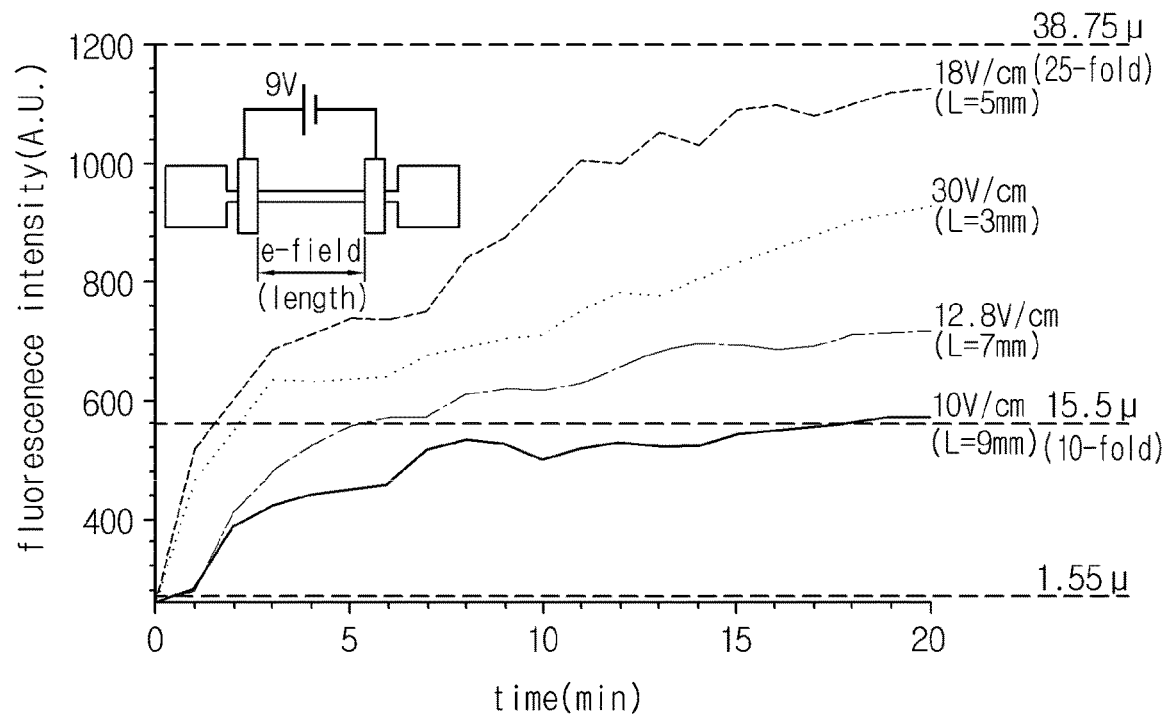
FIG. 10 is a drawing that illustrates fluorescence intensity depending on the electric field at a constant voltage applied to the preconcentration kit for a lateral flow assay strip according to one embodiment of the present invention.

FIG. 10 is a drawing that illustrates fluorescence intensity depending on the electric field at a constant voltage applied to the preconcentration kit for a lateral flow assay strip according to one embodiment of the present invention. Referring to FIG. 10, it was found that the maximum preconcentration rate was obtained in the preconcentration kit to which a specified electric field was applied within a predetermined range of the electric field. For instance, the highest preconcentration rate was observed in the preconcentration kit using 18 V/cm.

The lateral flow assay strip may further comprise a distance adjustment element for adjusting the distance between the multiple selective ion permeable membranes and displaying the distance.

Figure 11:
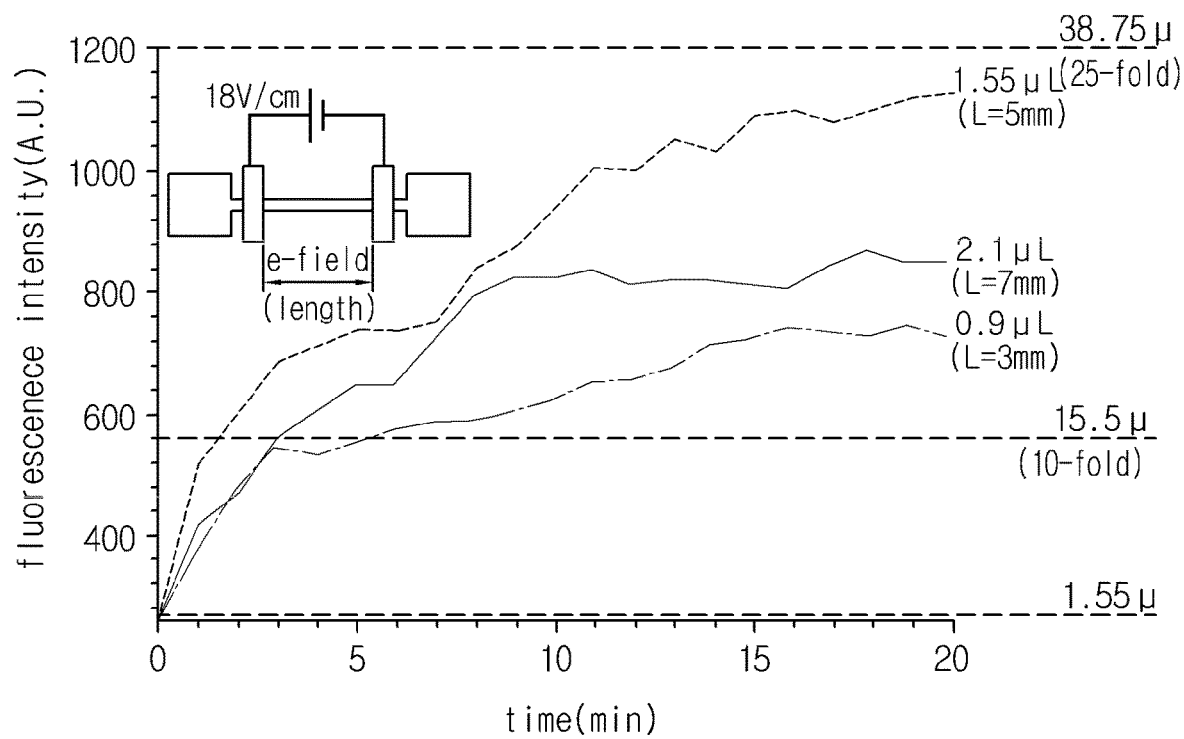
FIG. 11 is a drawing that illustrates fluorescence intensity depending on the distance at a constant electric field applied to the preconcentration kit for a lateral flow assay strip according to one embodiment of the present invention.

FIG. 11 is a drawing that illustrates fluorescence intensity depending on the distance at a constant electric field applied to the preconcentration kit for a lateral flow assay strip according to one embodiment of the present invention. Referring to FIG. 11, it was found that the maximum preconcentration rate was obtained in the preconcentration kit set to a specified distance within a predetermined range of the distances. For instance, the highest preconcentration rate was observed in the preconcentration kit set to a 5 mm distance.

In accordance with the embodiments of the present invention, the amounts of preconcentration can be appropriately adjusted depending on the analytes by constructing a matching table on the voltage, the electric field, the distance, etc. For example, it may be set to Voltage—9 V, Sample buffer—0.1× PBS, Time—10 min, Sample volume—20 uL, Detection time—within 3 min after conjugate pad connection, Electrode—Ag/AgCl electrode. It was further confirmed from additional experiments using urine in the experiment with PBS that urine is also available.

Figure 12:
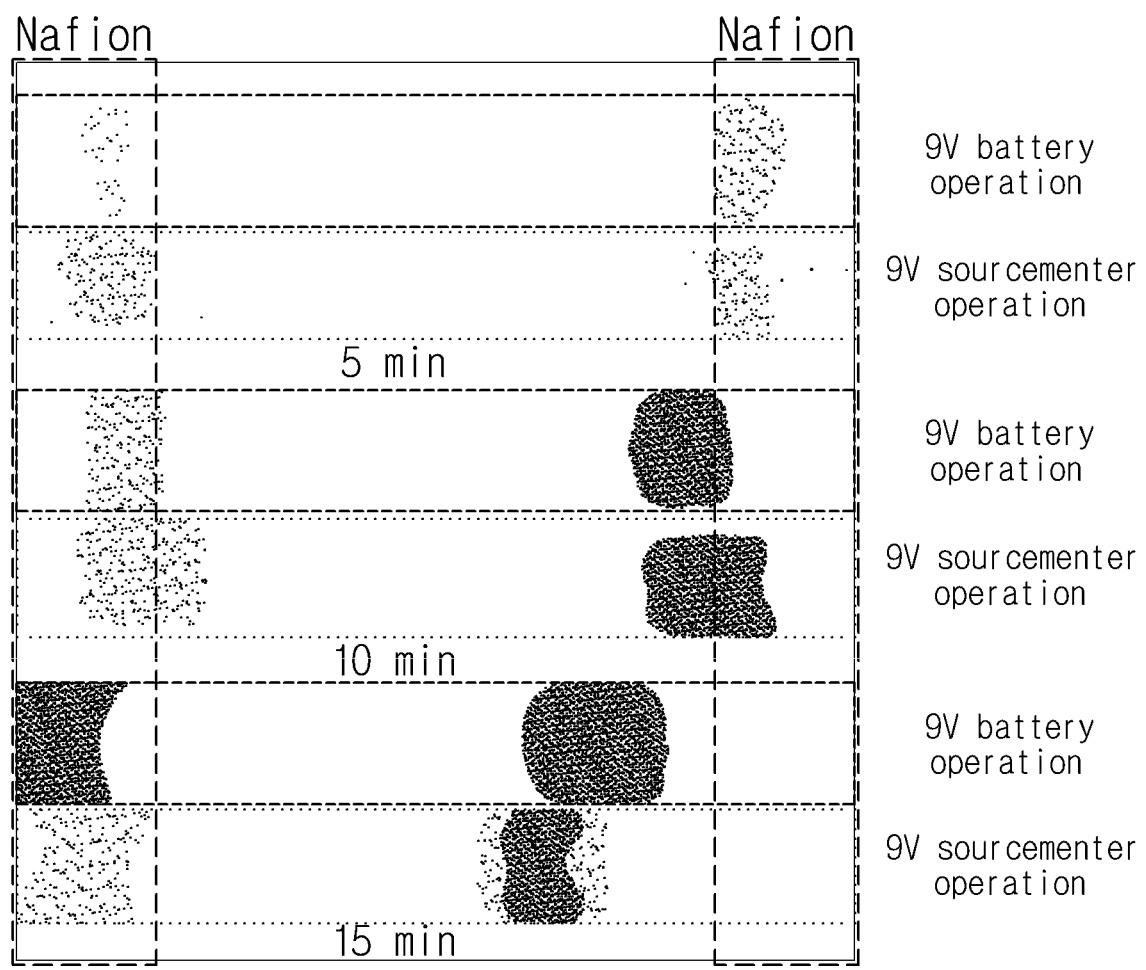
FIGS. 12 and 13 are the drawings that illustrate the results from the preconcentration of the analytes using source meters and batteries in a preconcentration kit for a lateral flow assay strip according to one embodiment of the present invention.
Figure 13:
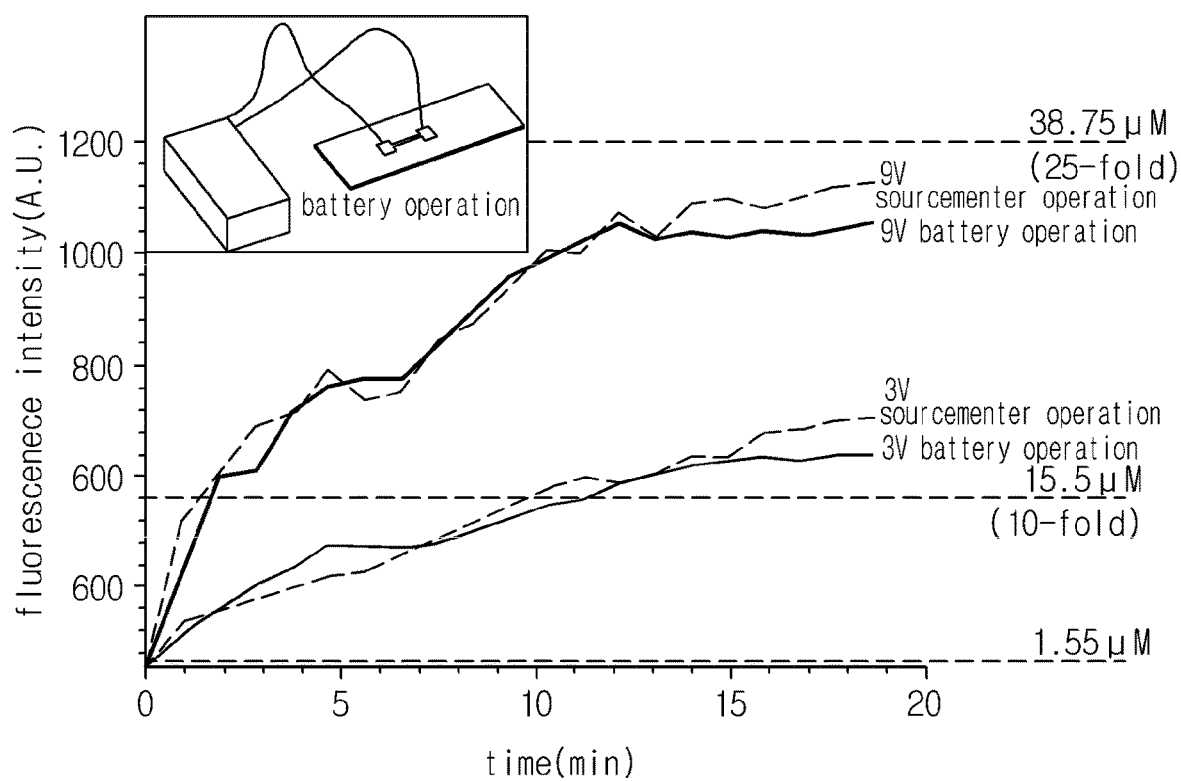

FIGS. 12 and 13 are the drawings that illustrate the results from the preconcentration of the analytes using source meters and batteries in the preconcentration kit for a lateral flow assay strip according to one embodiment of the present invention. Referring to FIGS. 12 and 13, it was shown that even with commercial batteries, the preconcentration kit has no problem in preconcentrating the analytes.

Figure 14:
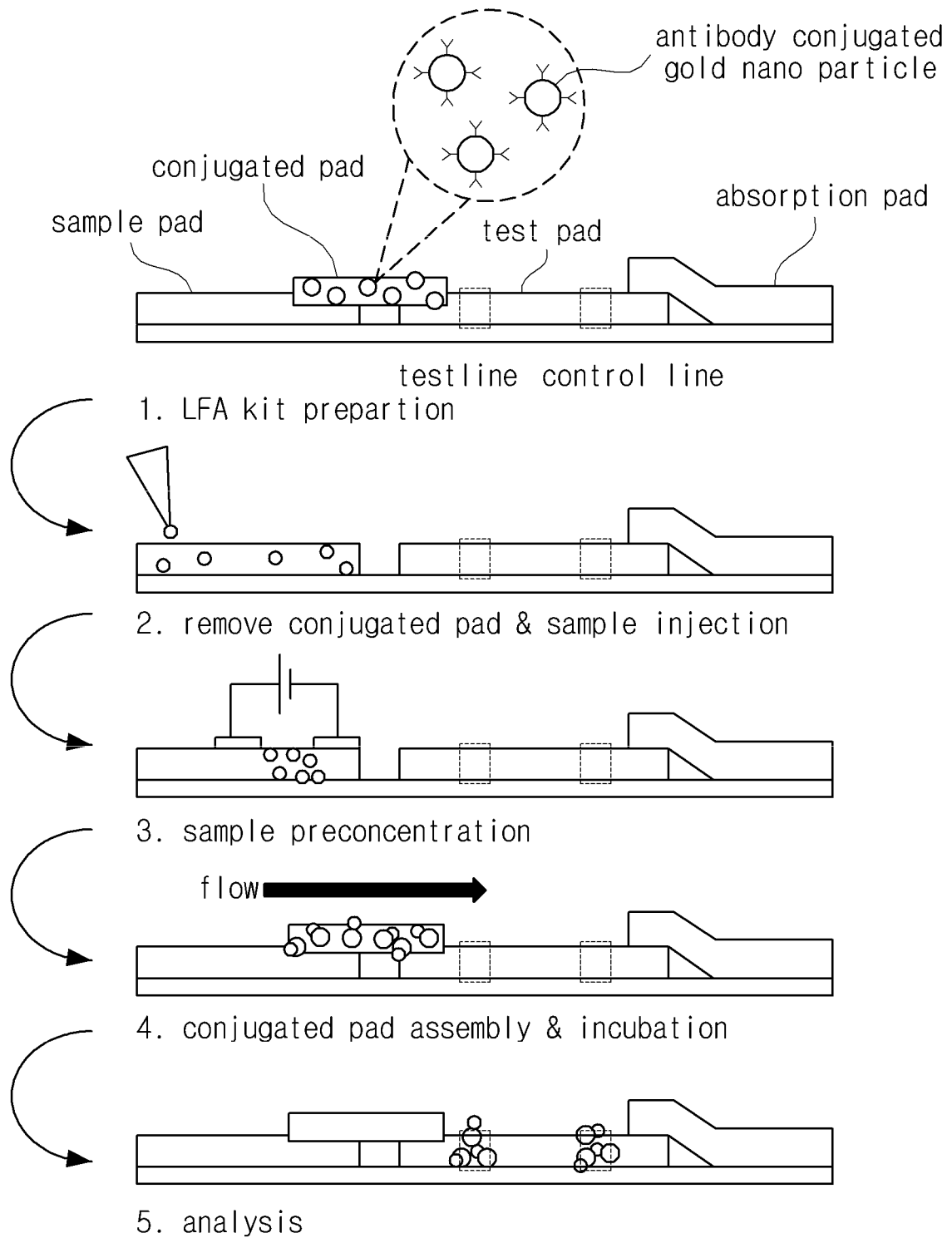
FIG. 14 is a drawing that illustrates a lateral flow assay method using a lateral flow assay strip according to another embodiment of the present invention.

FIG. 14 is a drawing that illustrates a lateral flow assay method using a lateral flow assay strip according to another embodiment of the present invention.

Referring to FIG. 14, a lateral flow assay strip is prepared. The conjugate pad is removed. The sample pad is injected with samples to be detected and preconcentrated. The preconcentration kit is attached to the sample pad. The samples are preconcentrated by applying the electric field to the preconcentrate kit. The electric field is turned off, and the conjugate pad is connected. The samples preconcentrated by a capillary action flow to the conjugate pad and react with receptors in nanoparticles. The samples reacted with the nanoparticles flow to the test pad and react with receptors on test lines and control lines. Finally, the test lines and the control lines are analyzed.

The lateral flow assay method using the lateral flow assay strip for detecting the analytes in a sample comprises injecting the sample into a sample pad, preconcentrating the analytes by attaching a preconcentrate kit to the sample pad, and transferring the analytes to a conjugate pad by connecting the conjugate pad to the sample pad.

The lateral flow assay method may further comprise removing the conjugate pad from the sample pad prior to injecting the sample into the sample pad. If the conjugate pad is not removed in advance, the analytes (sample) may flow to the detection region (test line) during the preconcentration stage, or the nanoparticles on the conjugate pad may flow to the control region (control line). In other words, the detection would be advanced during the preconcentration step, which could raise a reliability issue of the test itself.

The preconcentration of the analytes are carried out by applying the electric field to the preconcentration kit. The higher the electric field is, the higher the preconcentration rate can be obtained. However, at the high electric field, the analytes may be destroyed and the binding of the analytes with the receptors may not occur well. Also, the binding of the receptors with the nanoparticles may be collapsed at the high electric field.

Once the analytes are preconcentrated, the electric field applied to the preconcentration kit is removed and the conjugate pad is connected to the sample pad.

The lateral flow assay method may further comprise removing the preconcentration kit from the sample pad prior to connecting the conjugate pad to the sample pad.

The lateral flow assay method may provide a reservoir to the sample pad to maintain a fully wet condition. It may prevent the change of concentration resulting from the supply of more than a certain amount of sample or the evaporation of the sample and increase the preconcentration rate.

When the preconcentration is conducted in the lateral flow assay method, an electric field is applied to two nafions by applying a voltage.

In the lateral flow assay method, the electric field may be controlled by adjusting the distance between two nafions while retaining a constant voltage. The narrower distance may increase the electric field, resulting in the high ratio of preconcentration. However, the limit of the absolute amount of preconcentration of samples between two nafions may limit the preconcentration rate. Therefore, it is necessary to adjust the optimal amount of preconcentration according to the electric field.

The lateral flow assay method does not apply the electric field around the receptors (detectors). If the electric filed is applied to the regions where the receptors (detectors) exist, the receptors may be destroyed, or the combined receptors may be broken away. The ICP phenomena cannot be directly used in the test pad where the detection regions and the control regions are present as they destroy the Ab-Ag coupling due to the electric potential.

Figure 15:
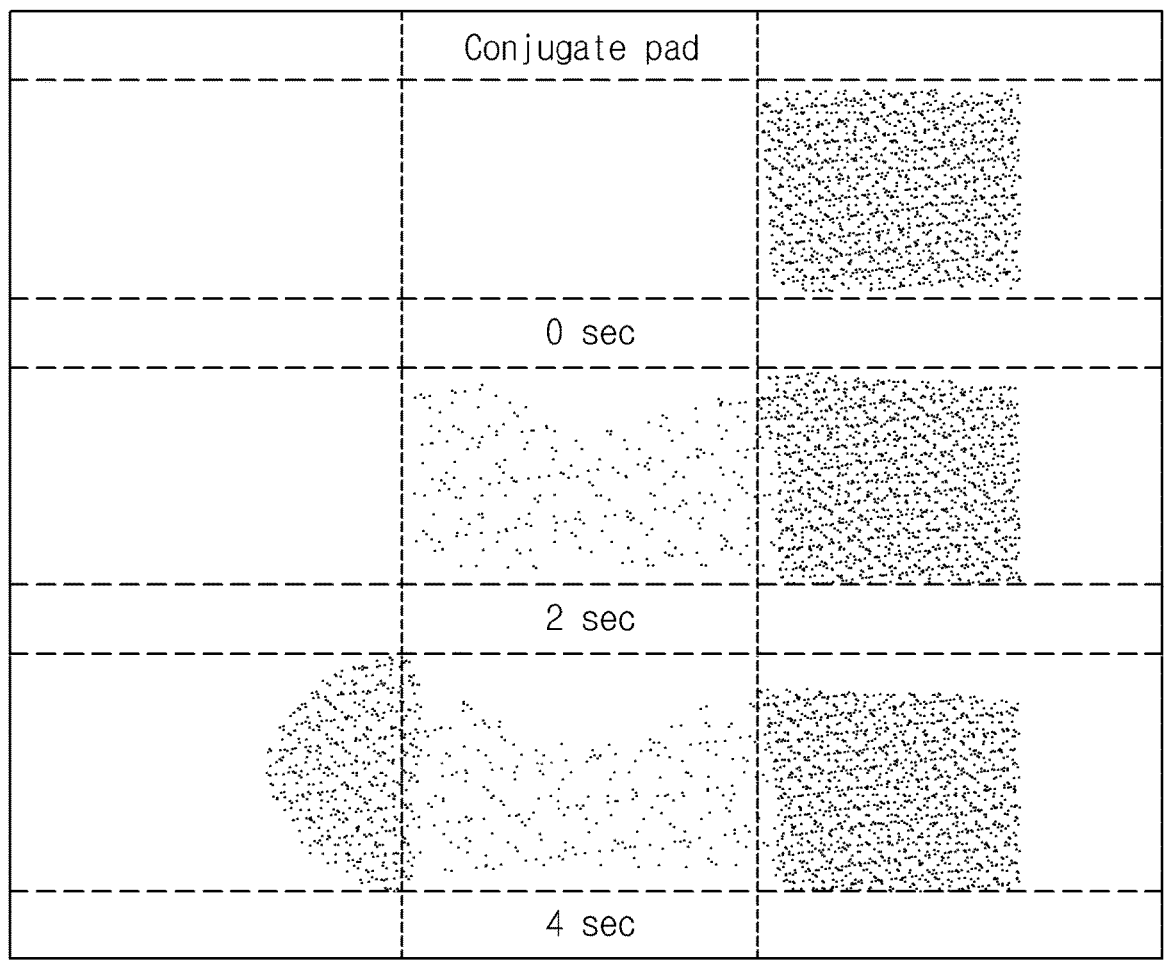
FIGS. 15 and 16 are the drawings that illustrate the flows of the preconcentrated analytes in a conjugate pad of a lateral flow assay strip according to one embodiment of the present invention.
Figure 16:
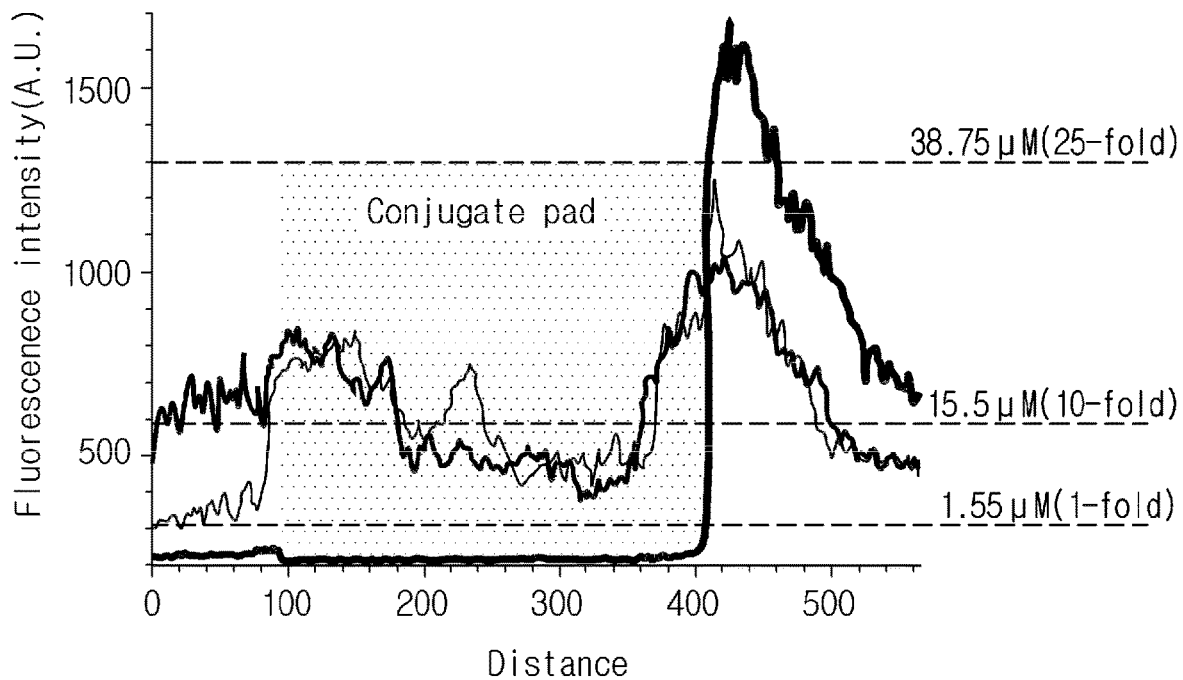

FIGS. 15 and 16 are the drawings that illustrate the flows of the preconcentrated analytes in a conjugate pad of a lateral flow assay strip according to one embodiment of the present invention. Referring to FIGS. 15 and 16, it can be understood that the preconcentrated analytes flowed in the conjugate pad.

Figure 17A:
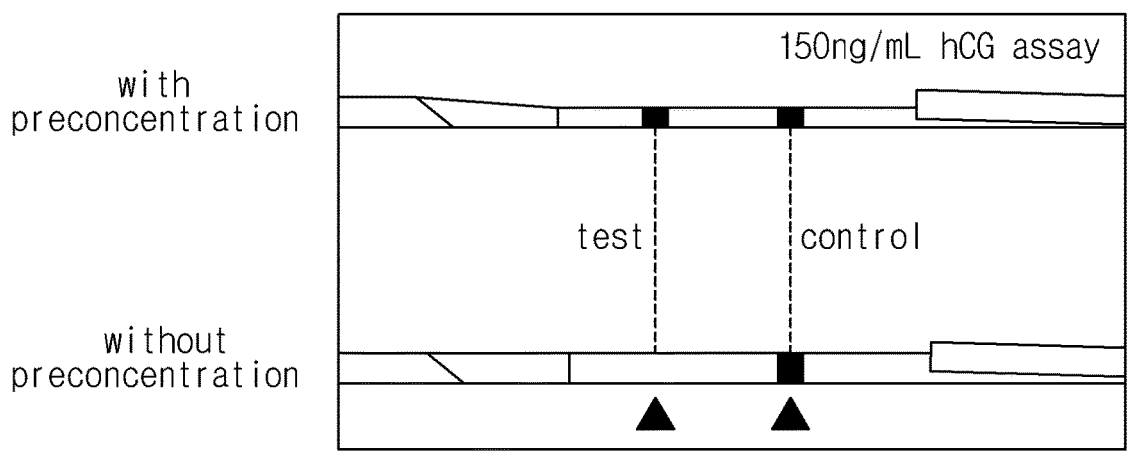
FIGS. 17a and 17b are the drawings that illustrate the detection results of the preconcentrated analytes and the non-preconcentrated analytes in a test pad of a lateral flow assay strip according to one embodiment of the present invention.
Figure 17B:
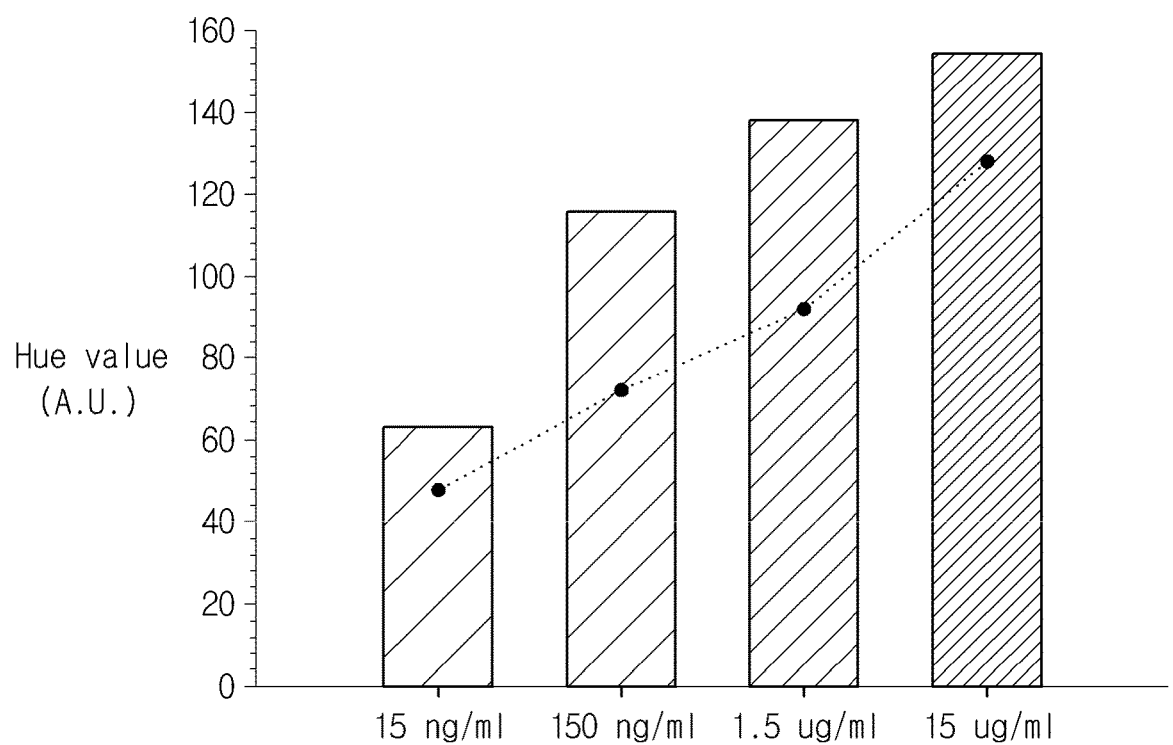

FIG. 17 is the drawings that illustrate the detection results of the preconcentrated analytes and the non-preconcentrated analytes in a test pad of a lateral flow assay strip according to one embodiment of the present invention.

It was observed that a conventional strip without the preconcentration kit did not show the test line, but in the strip with the preconcentration kit according to the embodiments of the present invention, the test line appeared. The dotted graph corresponds to the data for the conventional strip, and the bar graph indicates the data for the strip containing the preconcentration kit according to the embodiments of the present invention.

In the embodiments of the present invention, there are the effects that biomarkers which would be not detectable by conventional strips can be detected by means of separating the biomarkers as the analytes using ion concentration polarization (ICP) and preconcentrating the analytes at least several times. Biomarkers may be proteins as well as hormones such as human chorionic gonadotropin (HCG). For instance, various biomarkers including troponin as the myocardial infarction biomarker, amyloid beta as the Alzheimer's biomarker, and HER2 as the breast cancer biomarker may be preconcentrated for the improvement of sensitivity.

By using colorimetric methods, the analytes can be verified with the naked eyes. After the reaction, colors can be analyzed and quantified using images by taking pictures with a mobile phone. Intensity of the colors within the images may be measured or the hue value may be provided. Fluorometric methods are also available for quantitative analysis by applying fluorescent materials within the kit.

The embodiments of the present invention are provided to illustrate the technical idea of the present invention and in no way intended to be limiting the scope of the technical idea of the present invention. The scope of the present invention for which protection is sought shall be interpreted in accordance with the following claims, and all the equivalents thereof shall be construed to be within the scope of the present invention.

DESCRIPTION OF MARKS

| | |
|---|---|
| 100: Lateral Flow Assay Strip | 110: Support |
| 120: Sample Pad | 13: Preconcentration Kit |
| 130: Selective Ion Permeable Membrane | 140: Power |
| 150: Conjugate Pad | 160: Test Pad |
| 162: Detection Region | 164: Control Region |
| 170: Absorption Pad | |

It is claimed:

1. A lateral flow assay strip for detecting analytes in a sample, the lateral flow assay strip comprising:
   a support;
   a sample pad supported by the support and receiving the sample;
   a preconcentration kit supported by the support, the preconcentration kit comprising at least one selective ion permeable membrane, and electrodes connected to the at least one selective ion permeable membrane; and
   a test pad supported by the support and comprising a at least one captor for capturing the analytes.

2. The lateral flow assay strip of claim 1, characterized in that the preconcentration kit further comprises a channel in a linear form and a buffer formed apart from the channel, and the selective ion permeable membrane is configured to connect with the buffer and intersect with the channel.

3. The lateral flow assay strip of claim 2, characterized in that the selective ion permeable membrane exists in multiple numbers, and the multiple selective ion permeable membranes are separately located according to a flow direction of the lateral flow assay strip.

4. The lateral flow assay strip of claim 3, further comprising a distance adjustment element for adjusting a distance between the multiple selective ion permeable membranes and displaying the distance.

5. The lateral flow assay strip of claim 2, characterized in that the preconcentration kit further comprises a power supply connected to the electrodes.

6. The lateral flow assay strip of claim 5, further comprising a power adjustment element for adjusting an amount of electric power and displaying the amount of the adjusted power.

7. The lateral flow assay strip of claim 1, characterized in that the assaystrip is configured to be switched from (i) a first state which does not form a flow path of the analytes between the sample pad and the test pad to (ii) a second state that forms a flow path of the analytes between the sample pad and the test pad.

8. The lateral flow assay strip of claim 7, characterized in that the assaystrip further comprises a state switching element for switching the assaystrip from the first state to the second state, and the state switching element is operated in a manner of push, slide, turn, seesaw, removal of a barrier, or a combination thereof.

9. The lateral flow assay strip of claim 8, characterized in that the state switching element separates the preconcentration kit from the sample pad.

10. The lateral flow assay strip of claim 1, further comprising a conjugate pad which is connected to the test pad and comprises an assembly in which detectors that will bind to the analytes to produce conjugates are joined to indicators.

11. The lateral flow assay strip of claim 10, characterized in that the conjugate pad and the state switching element are configured in an integral body.

12. The lateral flow assay strip of claim 10, characterized in that the test pad comprises (i) a detection region comprising a first captor for capturing the conjugates and/or (ii) a control region comprising a second captor for capturing the assembly or detectors that failed to form the conjugates.

13. The lateral flow assay strip of claim 1, further comprising an absorption pad which is connected to the test pad and for absorbing the sample using a capillary action.

14. A lateral flow assay strip for detecting analytes in a sample, the lateral flow assay strip comprising:
- a support;
- a sample pad connected to the support and receiving the sample;
- a test pad connected to the support and comprising a captor for capturing the analytes;
- a preconcentration kit which comprises at least one selective ion permeable membrane, and electrodes connected to the at least one selective ion permeable membrane; and
- a case accommodating the lateral flow assay strip; and
- a state switching element configured to block and to connect a flow path of the analytes between the sample pad and the test pad, which is connected to the support, the sample pad, the test pad, or the case.

* * * * *